(12) United States Patent
Kim et al.

(10) Patent No.: US 8,889,267 B2
(45) Date of Patent: *Nov. 18, 2014

(54) ORGANIC LIGHT EMITTING DEVICE

(75) Inventors: Young-Kook Kim, Yongin (KR);
Seok-Hwan Hwang, Yongin (KR);
Yoon-Hyun Kwak, Yongin (KR);
Hye-Jin Jung, Yongin (KR);
Hyung-Jun Song, Yongin (KR); Jin-O Lim, Yongin (KR); Jong-Hyuk Lee, Yongin (KR)

(73) Assignee: Samsung Display Co., Ltd., Yongin-si (KR)

(*) Notice: Subject to any disclaimer, the term of this patent is extended or adjusted under 35 U.S.C. 154(b) by 211 days.

This patent is subject to a terminal disclaimer.

(21) Appl. No.: 12/873,088

(22) Filed: Aug. 31, 2010

(65) Prior Publication Data

US 2011/0057177 A1 Mar. 10, 2011

(30) Foreign Application Priority Data

Sep. 4, 2009 (KR) .................. 10-2009-0083508

(51) Int. Cl.
*H01L 51/50* (2006.01)
*C07D 471/04* (2006.01)
*C07D 417/04* (2006.01)
*C07D 401/14* (2006.01)
*C07D 403/10* (2006.01)
*C07D 487/04* (2006.01)
*C07D 403/04* (2006.01)
*C07D 209/60* (2006.01)
*C07D 519/00* (2006.01)
*C07D 413/10* (2006.01)

(52) U.S. Cl.
CPC ............ *C07D 403/10* (2013.01); *C07D 417/04* (2013.01); *C07D 401/14* (2013.01); *C07D 471/04* (2013.01); *C07D 487/04* (2013.01); *C07D 403/04* (2013.01); *C07D 209/60* (2013.01); *C07D 519/00* (2013.01); *C07D 413/10* (2013.01)
USPC ............................... 428/690; 546/121; 546/81

(58) Field of Classification Search
None
See application file for complete search history.

(56) References Cited

U.S. PATENT DOCUMENTS

| | | | |
|---|---|---|---|
| 5,645,948 A | 7/1997 | Shi et al. | |
| 8,344,365 B2 * | 1/2013 | Kim et al. | 257/40 |
| 2007/0252517 A1 * | 11/2007 | Owczarczyk et al. | 313/504 |
| 2008/0124455 A1 | 5/2008 | Shin et al. | |
| 2010/0249349 A1 * | 9/2010 | Chebotareva et al. | 526/259 |
| 2011/0037060 A1 * | 2/2011 | Kim et al. | 257/40 |

FOREIGN PATENT DOCUMENTS

| | | | | |
|---|---|---|---|---|
| JP | 2005-093159 A | 4/2005 | | |
| JP | 4025136 B2 | 10/2007 | | |
| JP | 2008-028424 A | 2/2008 | | |
| JP | 2010-073987 | 4/2010 | | |
| KR | 10-2007-0069158 A | 7/2007 | | |
| KR | 10-0743395 B1 | 7/2007 | | |
| KR | 10-2008-0047209 | 5/2008 | | |
| WO | WO 2007/090773 A1 * | 8/2007 | | C08G 61/00 |

OTHER PUBLICATIONS

KIPO Office action dated May 24, 2011 in priority Korean application No. 10-2009-0083508, 6 pps.
European Search Report dated Dec. 23, 2010, for corresponding European Patent application 10251547.5.
Mohanakrishnan, A., et al., *A one pot synthesis of annulated carbazole analogs*, Tetrahedron Letters, vol. 49, Jul. 9, 2008, pp. 5850-5854, XP-002612975.
Chinese Office action dated Dec. 26, 2013, for corresponding Chinese Patent application 201010272203.8, (6 pages).
EPO Office action dated Jul. 3, 2014, for corresponding European Patent application 10251547.5, (6 pages).
Martinez-Esperon, et al., *Coupling and cycloaddition of ynamides: homo- and Negishi coupling of tosylynamides and intramolecular [4+2] cycloaddition of N- (o-ethynl) phenyl ynamides and arylynamides*, DATABASE CAPLUS [Online], Chemical Abstracts Service, Columbus, Ohio, (2006), Database Accession No. 2006-284703, (2 pages).

Martinez-Esperon, et al., *Synthesis of carbazoles from ynamides by intramolecular dehydro Diels-Alder reactions*, DATABASE CAPLUS [Online], Chemical Abstracts Service, Columbus, Ohio, (2005), Database Accession No. 2005-396068, (2 pages).

Martinez-Esperon, et al., *Synthesis of carbazoles by dehydro Diels-Alder reactions of ynamides*, DATABASE CAPLUS [Online], Chemical Abstracts Service, Columbus, Ohio, (2008), Database Accession No. 2008-338897, (1 page).

Dhayalan, V., et al., *A versatile synthesis of annulated carbazole analogs involving a domino reaction of bromomethylindoles with arenes/heteroarenes*, DATABASE CAPLUS [Online], Chemical Abstracts Service, Columbus, Ohio, (2009), Database Accession No. 2009-168752, (2 pages).

\* cited by examiner

*Primary Examiner* — J. L. Yang

(74) *Attorney, Agent, or Firm* — Christie, Parker & Hale, LLP

(57) ABSTRACT

Embodiments of the present invention are directed to a heterocyclic compound and an organic light-emitting device including the heterocyclic compound. The heterocyclic compound is represented by Formula 1 or Formula 2. The organic light-emitting devices using the heterocyclic compounds have high-efficiency, low driving voltage, high luminance and long lifespan.

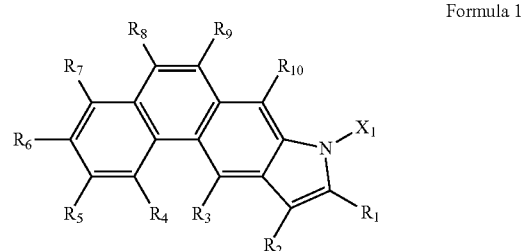

Formula 1

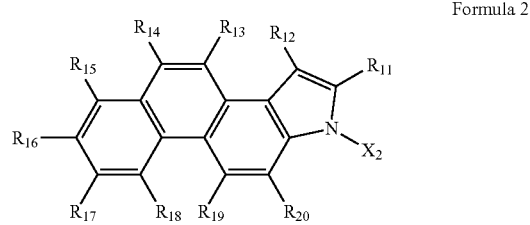

Formula 2

17 Claims, 1 Drawing Sheet

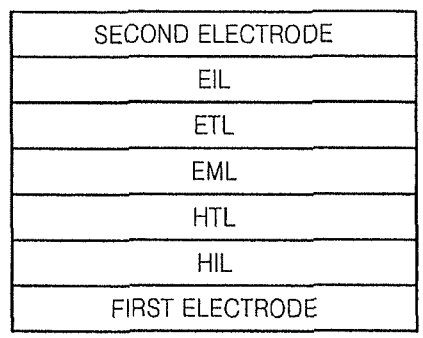

ORGANIC LIGHT EMITTING DEVICE

CROSS-REFERENCE TO RELATED PATENT APPLICATION

This application claims priority to and the benefit of Korean Patent Application No. 10-2009-0083508, filed on Sep. 4, 2009, in the Korean Intellectual Property Office, the entire content of which is incorporated herein by reference.

BACKGROUND OF THE INVENTION

1. Field of the Invention

The present invention relates to heterocyclic compounds and organic light-emitting devices including the heterocyclic compounds.

2. Description of the Related Art

Organic light-emitting devices are self-emission type display devices, and have wide viewing angles, high contrast ratios, and short response times. Due to these characteristics, organic light-emitting devices are drawing much attention.

Light-emitting devices can be roughly classified into inorganic light-emitting devices which include emission layers containing inorganic compounds, and organic light-emitting devices which include emission layers containing organic compounds. Organic light-emitting devices have higher luminance, lower driving voltages, and shorter response times than inorganic light-emitting devices. In addition, organic light-emitting devices produce various colors. Thus, research has been conducted into organic light-emitting devices.

Typically, an organic light-emitting device has a stack structure including an anode, a cathode and an organic emission layer between the anode and cathode. However, a hole injection layer and/or a hole transport layer may be further stacked between the anode and the organic emission layer, and/or an electron transport layer may be further stacked between the organic emission layer and the cathode. In other words, an organic light-emitting device may have an anode/hole transport layer/organic emission layer/cathode stack structure or an anode/hole transport layer/organic emission layer/electron transport layer/cathode stack structure.

As a material for forming the organic emission layer, a phenanthrene derivative can be used. However, organic light-emitting devices including known light-emitting materials do not have satisfactory life span, efficiency, or power consumption characteristics, thus leaving much room for improvement.

SUMMARY OF THE INVENTION

According to embodiments of the present invention, a heterocyclic compound has excellent electrical characteristics, charge transporting capabilities and light-emission capabilities.

In some embodiments of the present invention, an organic light-emitting device includes the heterocyclic compound.

In other embodiments of the present invention, a flat panel display device includes the organic light-emitting device.

According to some embodiments of the present invention, an organic light-emitting device includes at least one layer containing the heterocyclic compound, where the at least one layer is formed using a wet process.

According to embodiments of the present invention, a heterocyclic compound includes compounds represented by Formula 1 below:

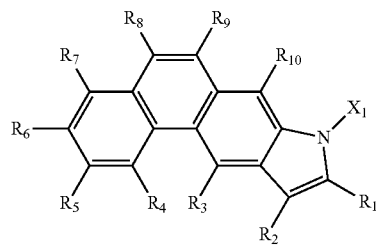

Formula 1

In Formula 1, $X_1$ is selected from substituted and unsubstituted $C_1$-$C_{50}$ alkyl groups, substituted and unsubstituted $C_3$-$C_{50}$ cycloalkyl groups, substituted and unsubstituted $C_6$-$C_{50}$ arylthio groups, substituted and unsubstituted $C_5$-$C_{60}$ aryl groups, amino groups substituted with at least one $C_6$-$C_{60}$ aryl group, substituted and unsubstituted $C_3$-$C_{60}$ heteroaryl groups, and substituted and unsubstituted $C_6$-$C_{60}$ condensed polycyclic groups. Each of $R_1$-$R_{10}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_6$-$C_{50}$ aryloxy groups, substituted and unsubstituted $C_6$-$C_{50}$ arylthio groups, substituted and unsubstituted $C_6$-$C_{60}$ aryl groups, amino groups substituted with at least one $C_6$-$C_{60}$ aryl group, substituted and unsubstituted $C_3$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_1$ through $R_{10}$ may optionally bond to each other, thereby forming an aromatic ring.

According to embodiments of the present invention, a heterocyclic compound includes a compound represented by Formula 2 below:

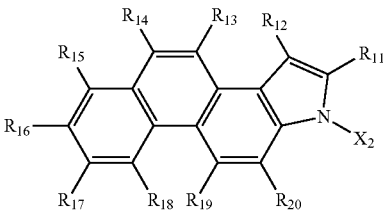

Formula 2

In Formula 2, $X_2$ is selected from substituted and unsubstituted $C_1$-$C_{50}$ alkyl groups, substituted and unsubstituted $C_3$-$C_{50}$ cycloalkyl groups, substituted and unsubstituted $C_6$-$C_{50}$ arylthio groups, substituted and unsubstituted $C_6$-$C_{60}$ aryl groups, amino groups substituted with at least one $C_6$-$C_{60}$ aryl group, substituted and unsubstituted $C_3$-$C_{60}$ heteroaryl groups, and substituted and unsubstituted $C_6$-$C_{60}$ condensed polycyclic groups. Each of $R_{11}$-$R_{20}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_6$-$C_{50}$ aryloxy groups, substituted and unsubstituted $C_6$-$C_{50}$ arylthio groups, substituted and unsubstituted $C_6$-$C_{60}$ aryl groups, amino groups substituted with at least one $C_6$-$C_{60}$ aryl group, substituted and unsubstituted $C_3$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_{11}$ through $R_{20}$ may optionally bond to each other, thereby forming an aromatic ring.

$R_6$ or $R_{16}$ may be independently selected from substituted and unsubstituted monocyclic to tetracyclic aryl groups, substituted and unsubstituted $C_3$-$C_{60}$ heteroaryl groups, and substituted and unsubstituted $C_6$-$C_{50}$ arylamine groups. Nonlimiting examples of suitable unsubstituted monocyclic to tetracyclic aryl groups, unsubstituted $C_3$-$C_{60}$ heteroaryl groups, and unsubstituted $C_6$-$C_{50}$ arylamine groups include unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups. Nonlimiting examples of suitable substituted monocyclic to tetracyclic aryl groups include phenyl groups, naphthyl groups, biphenyl groups, terphenyl groups, anthracenyl groups, fluorenyl groups, carbazolyl groups, and pyrenyl groups, that are substituted with at least one group selected from $C_1$-$C_5$ alkyl groups, $C_1$-$C_5$ alkoxy groups, cyano groups, amine groups, phenoxy groups, phenyl groups, and halogen groups. Nonlimiting examples of suitable substituted $C_3$-$C_{60}$ heteroaryl groups include those substituted with at least one group selected from $C_1$-$C_5$ alkyl groups, $C_1$-$C_5$ alkoxy groups, cyano groups, amine groups, phenoxy groups, phenyl groups, halogen groups, and $C_3$-$C_{60}$ heteroaryl groups. Nonlimiting examples of suitable substituted $C_6$-$C_{50}$ arylamine groups include those substituted with at least one group selected from $C_1$-$C_5$ alkyl groups, $C_1$-$C_4$ alkoxy groups, cyano groups, amine groups, phenoxy groups, phenyl groups, and halogen groups.

Each of $X_1$ and $X_2$ may be independently selected from substituted and unsubstituted monocyclic to tetracyclic aryl groups, and substituted and unsubstituted $C_3$-$C_{60}$ heteroaryl groups. Nonlimiting examples of suitable unsubstituted monocyclic to tetracyclic aryl groups and substituted $C_3$-$C_{60}$ heteroaryl groups include unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups. Nonlimiting examples of suitable substituted monocyclic to tetracyclic aryl groups include phenyl groups, naphthyl groups, biphenyl groups, terphenyl groups, anthracenyl groups, fluorenyl groups, carbazolyl groups, and pyrenyl groups, that are substituted with at least one group selected from $C_1$-$C_5$ alkyl groups, $C_1$-$C_5$ alkoxy groups, cyano groups, amine groups, phenoxy groups, phenyl groups, and halogen groups. Nonlimiting examples of suitable substituted $C_3$-$C_{60}$ heteroaryl group include those substituted with at least one group selected from $C_1$-$C_5$ alkyl groups, $C_1$-$C_5$ alkoxy groups, cyano groups, amine groups, phenoxy groups, phenyl groups, halogen groups, and $C_5$-$C_{10}$ heteroaryl groups.

Each of $R_1$, $R_2$, $R_{11}$ and $R_{12}$ may be independently selected from methyl groups and phenyl groups.

The heterocyclic compound of Formula 1 or Formula 2 may include one of Compounds 10, 17, 27, 33 and 42 below:

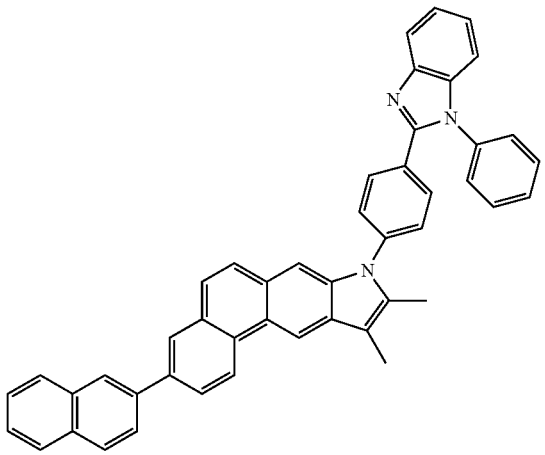

10

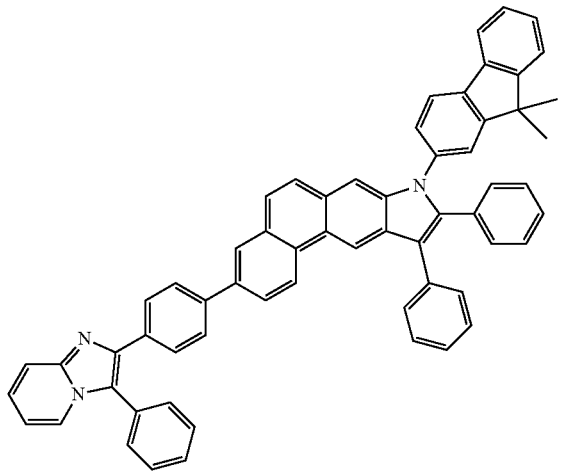

17

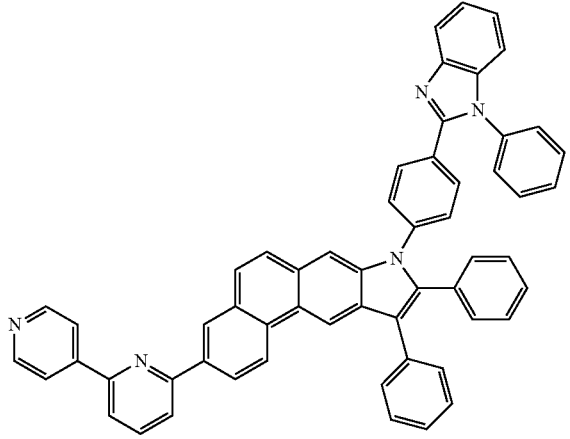

27

-continued

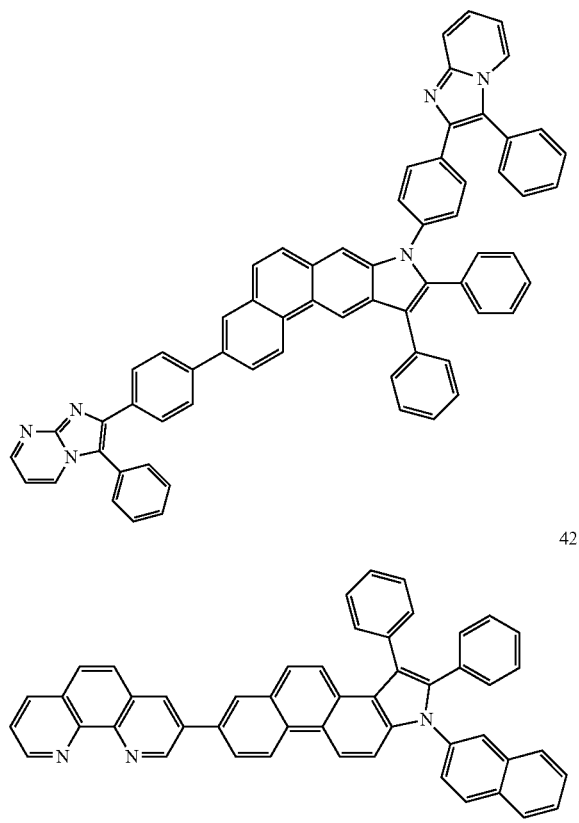

According to embodiments of the present invention, an organic light-emitting device includes a first electrode, a second electrode, and an organic layer between the first and second electrodes. The organic layer may include at least one layer including the heterocyclic compound described above.

The organic layer may include an electron injection layer or an electron transport layer.

The organic layer may include a single film having both an electron injection function and an electron transport function.

The organic layer may include an emission layer.

The organic layer may include an emission layer, and the heterocylic compound may be used as a fluorescent or phosphorescent host.

The organic layer may include an emission layer, and the heterocyclic compound may be used as a fluorescent dopant.

The organic layer may include an emission layer, and an electron injection layer or an electron transport layer, and the emission layer may include an anthracene compound.

The organic layer may include an emission layer, and an electron injection layer or an electron transport layer, and the emission layer may include an arylamine compound.

The organic layer may include an emission layer, and an electron injection layer or an electron transport layer, and the emission layer may include a styryl compound.

The organic layer may include an emission layer, and an electron injection layer or an electron transport layer, and the emission layer may include a red emission layer, a green emission layer, a blue emission layer, or a white emission layer, each of which may include a phosphorescent compound.

The organic layer may include at least one layer selected from a hole injection layer, a hole transport layer, an electron blocking layer, an emission layer, a hole blocking layer, an electron transport layer, and an electron injection layer.

The organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

According to embodiments of the present invention, a flat panel display device includes the organic light-emitting device described above, where the first electrode of the organic light-emitting device is electrically connected to a source electrode or a drain electrode of a thin-film transistor.

According to embodiments of the present invention, an organic light-emitting display includes the organic light-emitting device described above, where the at least one layer including the heterocyclic compound may be formed using a wet process.

BRIEF DESCRIPTION OF THE DRAWING

The above and other features and advantages of the present invention will become more apparent by reference to the following detailed description when considered in conjunction with the attached drawing in which:

FIG. 1 illustrates the structure of an organic light-emitting device according to an embodiment of the present invention.

DETAILED DESCRIPTION OF THE INVENTION

The present invention will now be described with reference to the accompanying drawings, in which exemplary embodiments of the invention are shown.

A heterocyclic compound according to an embodiment of the present invention is represented by Formula 1 below:

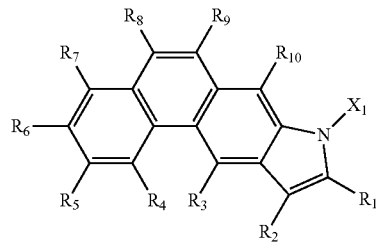

Formula 1

In Formula 1, $X_1$ may be selected from substituted and unsubstituted $C_1$-$C_{50}$ alkyl groups, substituted and unsubstituted $C_3$-$C_{50}$ cycloalkyl groups, substituted and unsubstituted $C_6$-$C_{50}$ arylthio groups, substituted and unsubstituted $C_6$-$C_{60}$ aryl groups, amino groups substituted with at least one $C_6$-$C_{60}$ aryl group, substituted and unsubstituted $C_3$-$C_{60}$ heteroaryl groups, and substituted and unsubstituted $C_6$-$C_{60}$ condensed polycyclic groups. Each of $R_1$-$R_{10}$ may be independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_4$-$C_{50}$ aryloxy groups, substituted and unsubstituted $C_6$-$C_{50}$ arylthio groups, substituted and unsubstituted $C_6$-$C_{60}$ aryl groups, amino groups substituted with at least one $C_6$-$C_{60}$ aryl group, substituted and unsubstituted $C_3$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_1$ through $R_{10}$ may optionally bond to each other, thereby forming an aromatic ring.

A heterocyclic compound according to another embodiment of the present invention is represented by Formula 2 below:

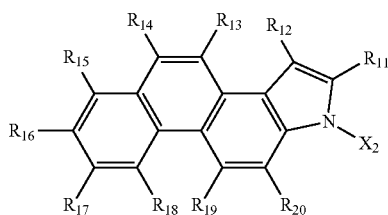

Formula 2

In Formula 2, $X_2$ is selected from substituted and unsubstituted $C_1$-$C_{50}$ alkyl groups, substituted and unsubstituted $C_3$-$C_{50}$ cycloalkyl groups, substituted and unsubstituted $C_6$-$C_{50}$ arylthio groups, substituted and unsubstituted $C_6$-$C_{60}$ aryl groups, amino groups substituted with at least one $C_6$-$C_{60}$ aryl group, substituted and unsubstituted $C_3$-$C_{60}$ heteroaryl groups, and substituted and unsubstituted $C_6$-$C_{60}$ condensed polycyclic groups. Each of $R_{11}$-$R_{20}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_6$-$C_{50}$ aryloxy groups, substituted and unsubstituted $C_6$-$C_{50}$ arylthio groups, substituted and unsubstituted $C_6$-$C_{60}$ aryl groups, amino groups substituted with at least one $C_6$-$C_{60}$ aryl group, substituted and unsubstituted $C_3$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_{11}$ through $R_{20}$ may optionally bond to each other, thereby forming an aromatic ring.

Nonlimiting examples of materials suitable for forming an emission layer or electron transport layer of an organic light-emitting device include Alq$_3$, 2,2',2"-(1,3,5-phenylene)tris-(1-phenyl)-1H-benzimidazole (TPBI), 2-Biphenyl-4-yl-5-(4-tert-butyl-phenyl)-[1,3,4]oxadiazole (PBD), perfluorinated compound (PF-6P), and 2,5-bis(6'-(2',2"-bipyridyl))-1,1-dimethyl-3,4-diphenylsilylol (PyPySPyPy). However, an organic light-emitting device manufactured using such materials does not have satisfactory lifespan, efficiency, and power consumption characteristics, leaving much room for improvement.

An organic light-emitting device manufactured using the heterocyclic compound of Formula 1 or Formula 2 (in which a phenanthrene group and an indole group are fused with each other) has good durability when stored or operated. In addition, due to the introduction of a substituent such as a fluorene group or a naphthyl group, molecular films may be maintained in good condition, thereby improving the characteristics of the organic light-emitting device.

The substituents in the heterocyclic compounds of Formulae 1 and 2 will now be described. $R_6$ or $R_{16}$ may be independently selected from substituted and unsubstituted monocyclic to tetracyclic aryl groups, substituted and unsubstituted $C_3$-$C_{60}$ heteroaryl groups, and substituted and unsubstituted $C_6$-$C_{50}$ arylamine groups. Nonlimiting examples of suitable unsubstituted monocyclic to tetracylic aryl groups, unsubstituted $C_3$-$C_{60}$ heteroaryl groups, and unsubstituted $C_6$-$C_{50}$ arylamine groups include unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups. Nonlimiting examples of suitable substituted monocyclic to tetracyclic aryl groups include phenyl groups, naphthyl groups, biphenyl groups, terphenyl groups, anthracenyl groups, fluorenyl groups, carbazolyl groups, and pyrenyl groups, that are substituted with at least one group selected from $C_1$-$C_5$ alkyl groups, $C_1$-$C_5$ alkoxy groups, cyano groups, amine groups, phenoxy groups, phenyl groups, and halogen groups. Nonlimiting examples of suitable substituted $C_3$-$C_{60}$ heteroaryl groups include those substituted with at least one group selected from $C_1$-$C_5$ alkyl groups, $C_1$-$C_5$ alkoxy groups, cyano groups, amine groups, phenoxy groups, phenyl groups, halogen groups, and $C_5$-$C_{10}$ heteroaryl groups. Nonlimiting examples of suitable substituted $C_6$-$C_{50}$ arylamine groups include those substituted with at least one group selected from $C_1$-$C_5$ alkyl groups, $C_1$-$C_4$ alkoxy groups, cyano groups, amine groups, phenoxy groups, phenyl groups, and halogen groups.

In the heterocyclic compound, each of $X_1$ and $X_2$ may be independently selected from substituted and unsubstituted monocyclic to tetracyclic aryl groups, and substituted and unsubstituted $C_3$-$C_{60}$ heteroaryl groups. Nonlimiting examples of suitable unsubstituted monocyclic to tetracyclic aryl groups and unsubstituted $C_3$-$C_{60}$ heteroaryl groups include unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups. Nonlimiting examples of substituted monocyclic to tetracyclic aryl groups include phenyl groups, naphthyl groups, biphenyl groups, terphenyl groups, anthracenyl groups, fluorenyl groups, carbazolyl groups, and pyrenyl groups, that are substituted with at least one group selected from $C_1$-$C_5$ alkyl groups, $C_1$-$C_5$ alkoxy groups, cyano groups, amine groups, phenoxy groups, phenyl groups, and halogen groups. Nonlimiting examples of substituted $C_3$-$C_{60}$ heteroaryl groups include those substituted with at least one group selected from $C_1$-$C_5$ alkyl groups, $C_1$-$C_5$ alkoxy groups, cyano groups, amine groups, phenoxy groups, phenyl groups, halogen groups, and $C_5$-$C_{10}$ heteroaryl groups.

With regard to Formulae 1 and 2, $R_1$, $R_2$, $R_{11}$ and $R_{12}$ may be each independently a methyl group or a phenyl group.

Hereinafter, substituents described with reference to Formulae 1 and 2 will now be described in detail.

In Formulae 1 and 2, the unsubstituted $C_1$-$C_{50}$ alkyl group may be linear or branched. Nonlimiting examples of the unsubstituted alkyl group include methyl groups, ethyl groups, propyl groups, isobutyl groups, sec-butyl groups, pentyl groups, iso-amyl groups, hexyl groups, heptyl groups, octyl groups, nonanyl groups, and dodecyl groups. At least one hydrogen atom of the alkyl group may be substituted with a substituent selected from heavy hydrogen atoms, halogen atoms, hydroxyl groups, nitro groups, cyano groups, amino groups, amidino groups, hydrazines, hydrazones, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

In Formulae 1 and 2, the unsubstituted $C_3$-$C_{50}$ cycloalkyl group refers to a $C_3$-$C_{50}$ alkyl group having a cyclic form. In the unsubstituted $C_3$-$C_{50}$ cycloalkyl group, one or more hydrogen atoms may be substituted with a substituent such as those described above with respect to the unsubstituted $C_1$-$C_{50}$ alkyl group.

In Formulae 1 and 2, the unsubstituted $C_1$-$C_{50}$ alkoxy group is a group having a —OA structure where A is an unsubstituted $C_1$-$C_{50}$ alkyl group as described above. Nonlimiting examples of the unsubstituted $C_1$-$C_{50}$ alkoxy group include methoxy groups, ethoxy groups, propoxy groups, isopropyloxy groups, butoxy groups, and pentoxy groups. At least one hydrogen atom of the alkoxy group may be substituted with a substituent such as those described above with respect to the alkyl group.

In Formulae 1 and 2, the unsubstituted $C_6$-$C_{60}$ aryl group refers to a carbocyclic aromatic system containing at least one ring. At least two rings may be fused to each other or linked to each other by a single bond. As used herein, the term "aryl" refers to an aromatic system, such as a phenyl, naphthyl, or anthracenyl system. At least one hydrogen atom in the aryl group may be substituted with a substituent such as those described above with respect to the unsubstituted $C_1$-$C_{50}$ alkyl group.

Nonlimiting examples of the substituted or unsubstituted $C_6$-$C_{60}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-toryl groups, o-, m-, and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

In Formulae 1 and 2, the unsubstituted $C_3$-$C_{60}$ heteroaryl group includes one, two or three hetero atoms selected from N, O, P and S. If the unsubstituted $C_3$-$C_{60}$ heteroaryl group has at least two rings, the rings may be fused to each other or linked to each other by a single bond. Nonlimiting examples of the unsubstituted $C_3$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. In addition, at least one hydrogen atom in the heteroaryl group may be substituted with a substituent such as those described above with respect to the unsubstituted $C_1$-$C_{50}$ alkyl group.

In Formulae 1 and 2, the unsubstituted $C_6$-$C_{50}$ aryloxy group is represented by —$OA_1$ where $A_1$ represents a substituent such as those described above with respect to the $C_6$-$C_{60}$ aryl group (except that the number of carbon atoms may be different). Nonlimiting examples of the aryloxy group include phenoxy groups. At least one hydrogen atom in the aryl group may be substituted with a substituent such as those described above with respect to the unsubstituted $C_1$-$C_{50}$ alkyl group.

In Formulae 1 and 2, the unsubstituted $C_6$-$C_{50}$ arylthiol group is represented by —$SA_1$ where $A_1$ represents a substituent such as those described above with respect to the $C_6$-$C_{60}$ aryl group (except that the number of carbon atoms may be different). Nonlimiting examples of the arylthiol group include benzenethiol groups, naphthylthiol groups, and fluorenylthiol groups. At least one hydrogen atom in the arylthiol group may be substituted with a substituent such as those described above with respect to the unsubstituted $C_1$-$C_{50}$ alkyl group.

In Formulae 1 and 2, the unsubstituted $C_6$-$C_{60}$ condensed polycyclic group refers to a substituent including at least two rings wherein at least one aromatic ring and/or at least one non-aromatic ring are fused to each other. The unsubstituted $C_6$-$C_{60}$ condensed polycyclic group may include one or more of the substituents described above with respect to the aryl group or heteroaryl group.

In Formulae 1 and 2, the $C_6$-$C_{50}$ arylamine group is an alternative expression of an amino group substituted with a $C_6$-$C_{50}$ aryl group, and if the $C_6$-$C_{50}$ arylamine group is substituted, the substitution occurs at an aryl group therein. Nonlimiting examples of the heterocyclic compound of Formula 1 or Formula 2 include Compounds 1 through 52 represented below. However, the heterocyclic compound of Formula 1 or Formula 2 is not limited thereto.

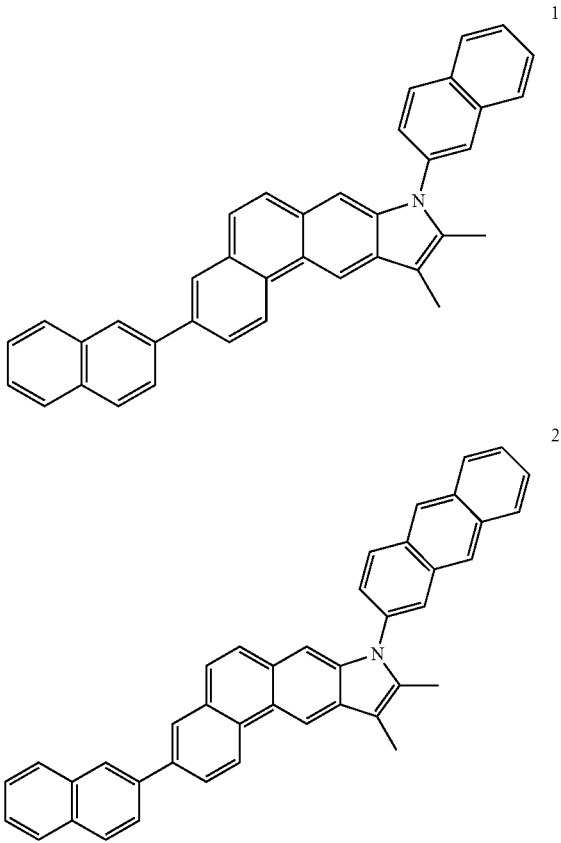

3
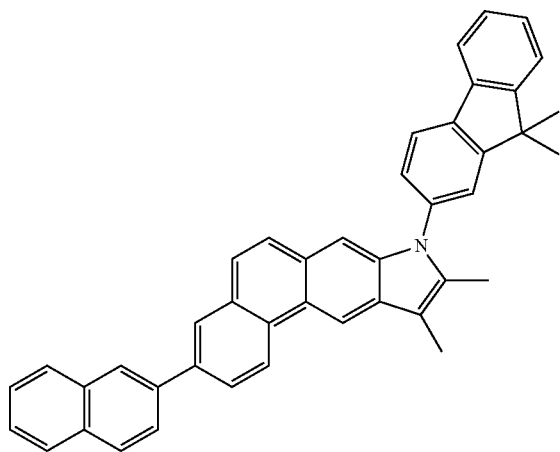
6
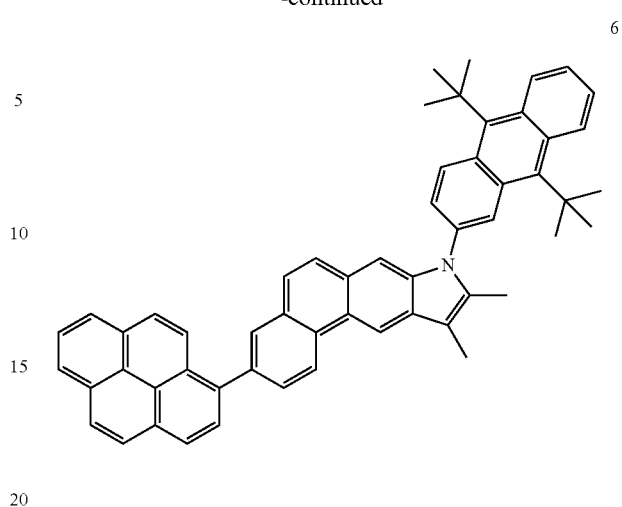
4
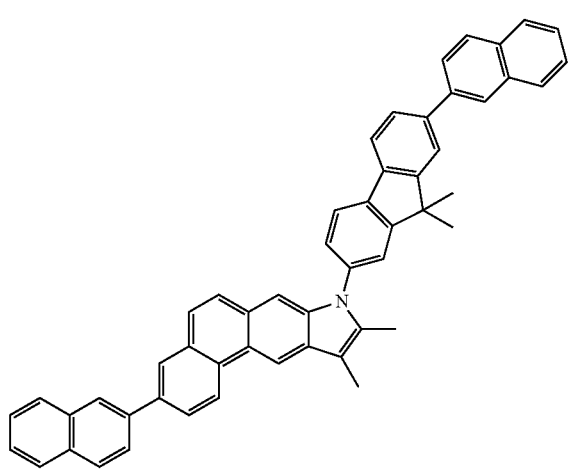
7
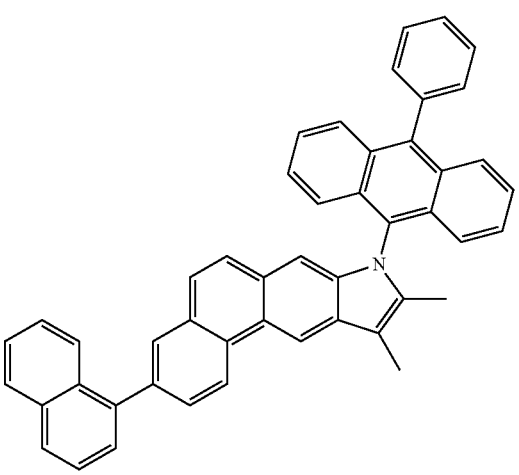
5
8
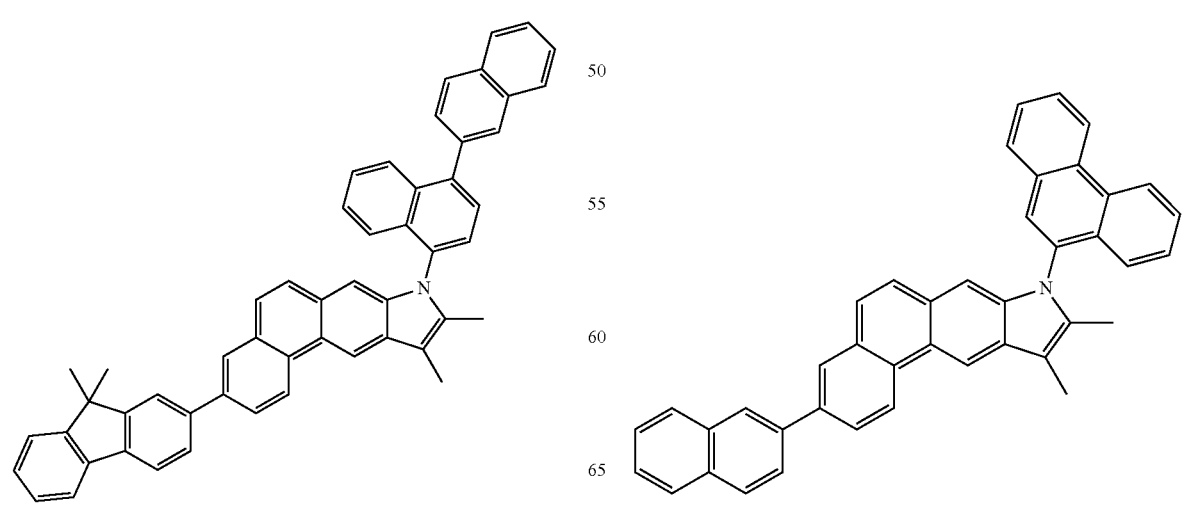

9
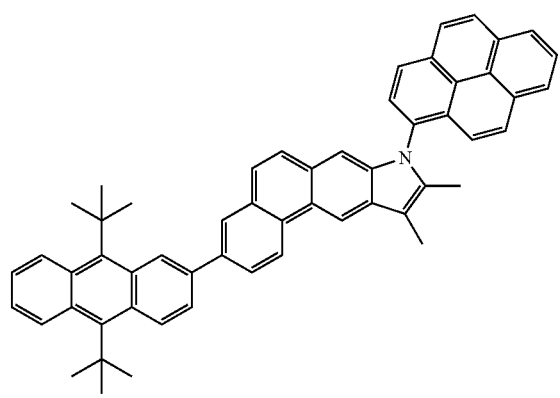
10
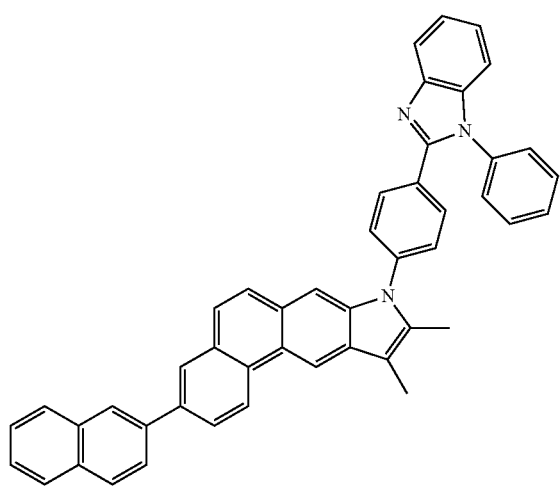
11
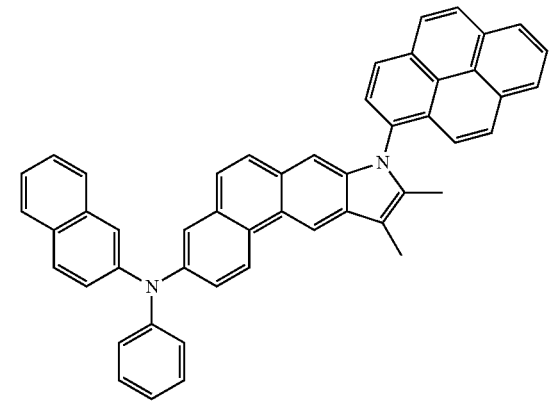
12
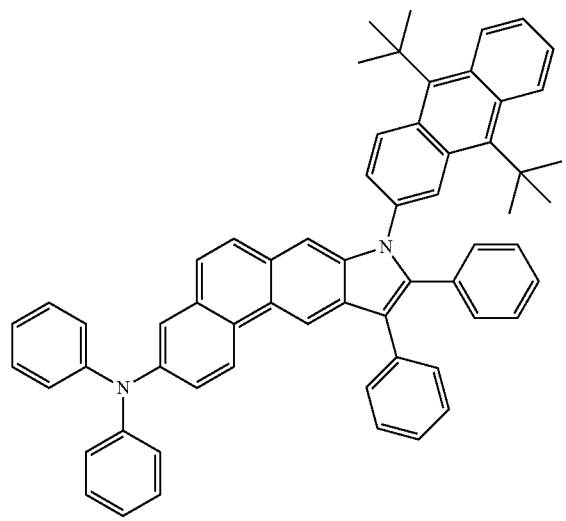
13
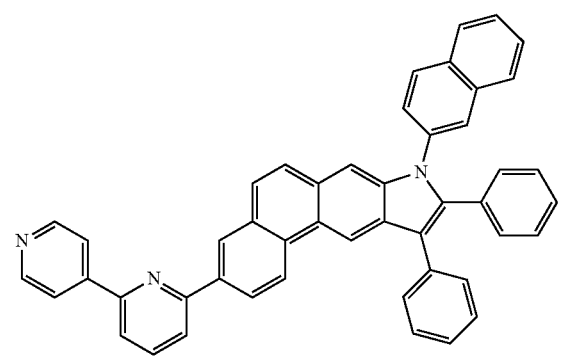
14
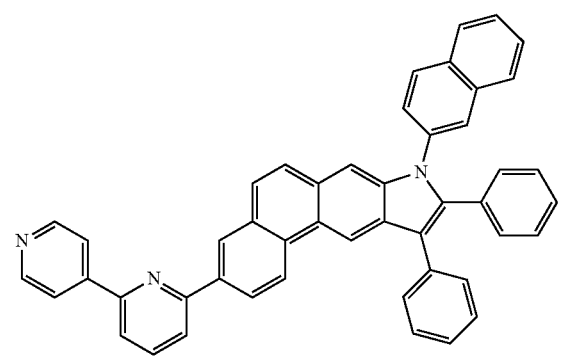

15
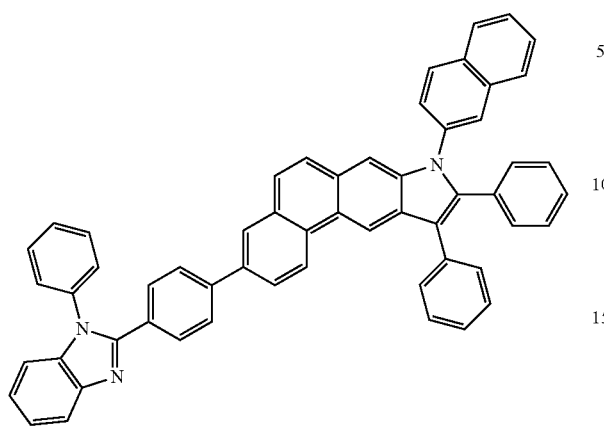
16
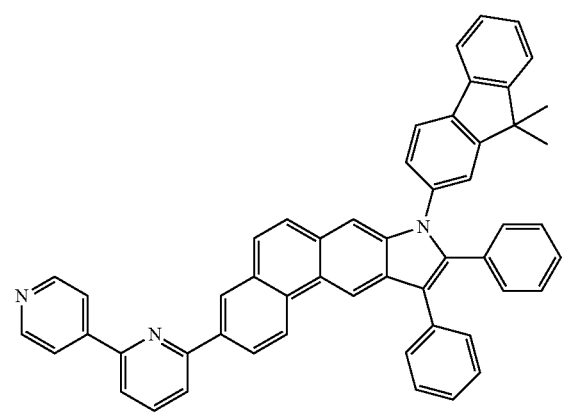
17
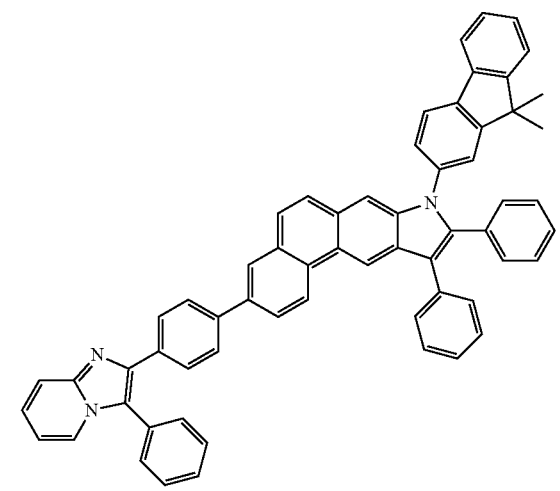
18
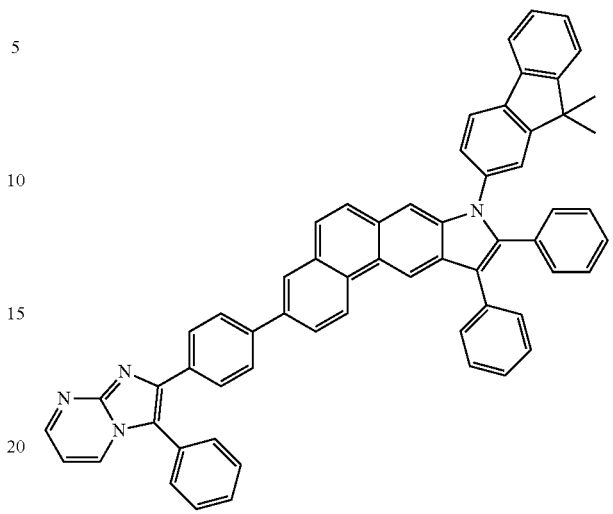
19
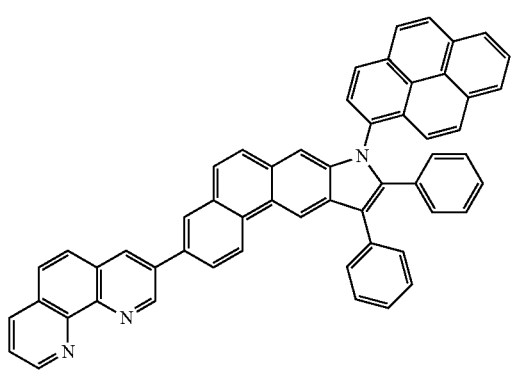
20
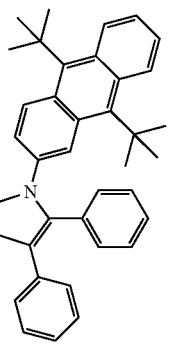

21
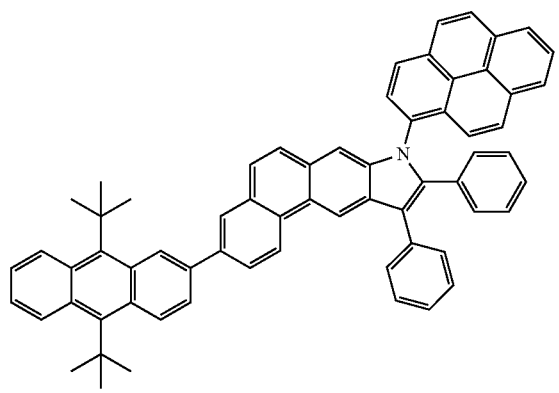
22
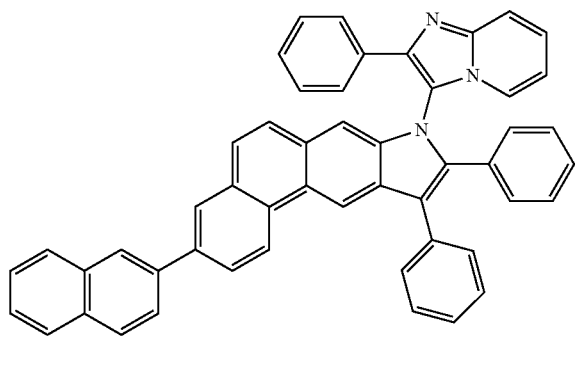
23
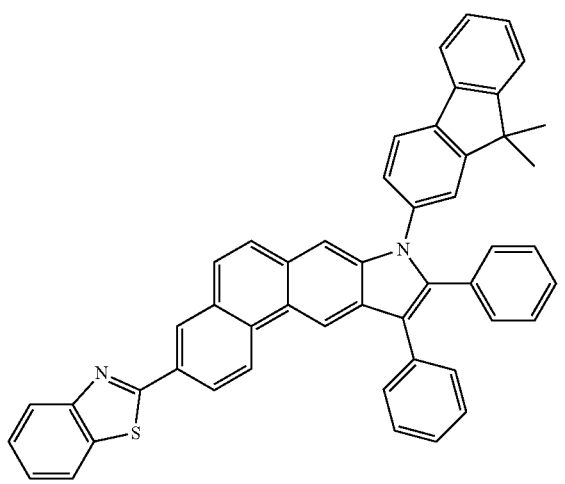
24
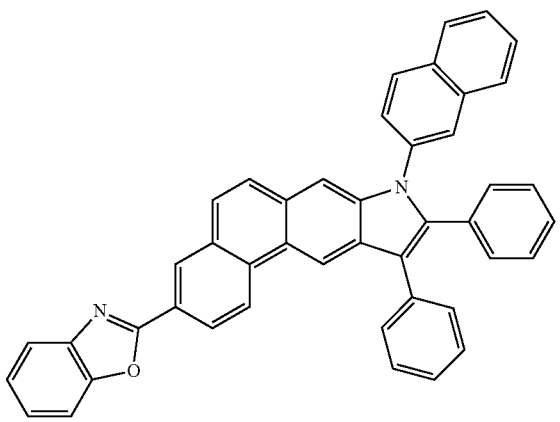
25
25
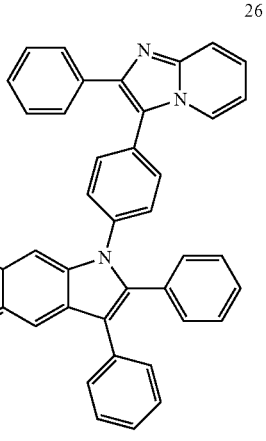
26

-continued
27
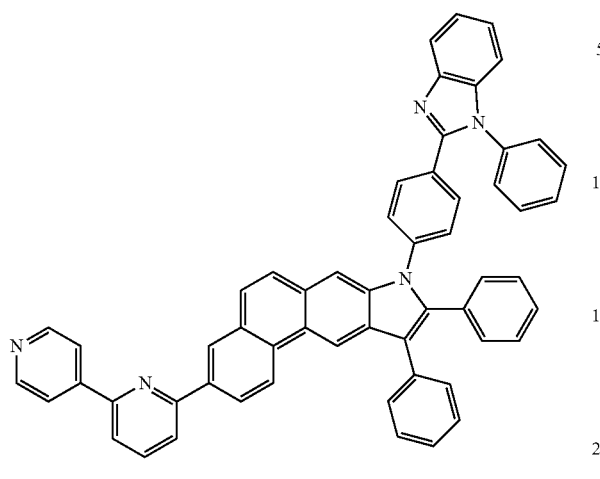
28
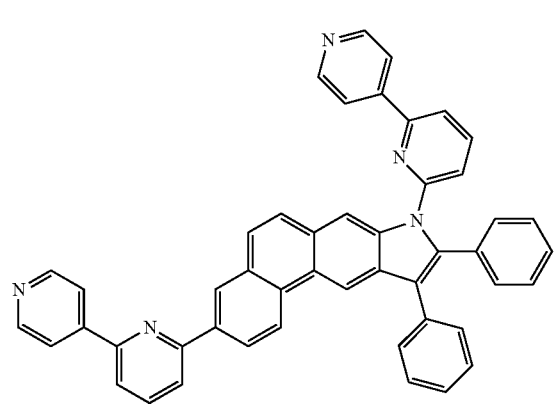
29
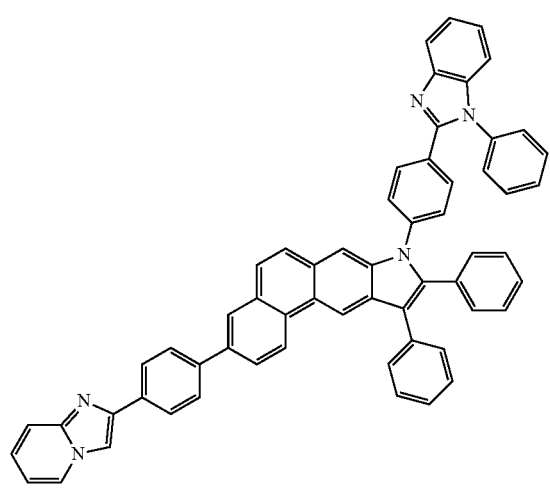
-continued
30
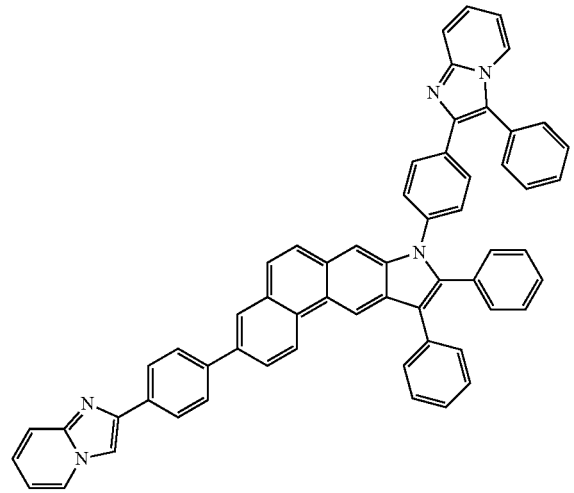
31
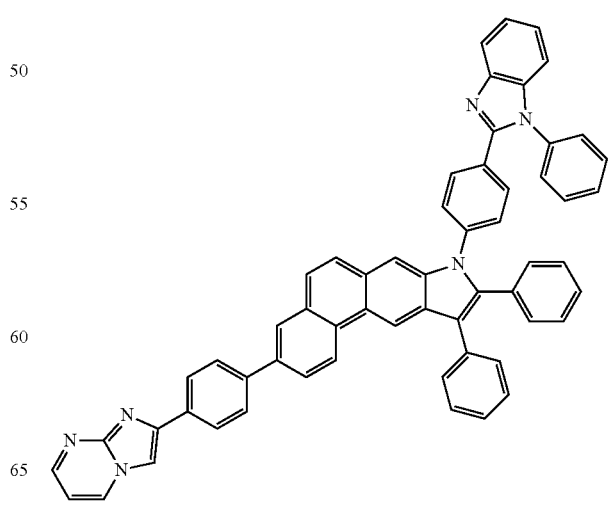
32

33
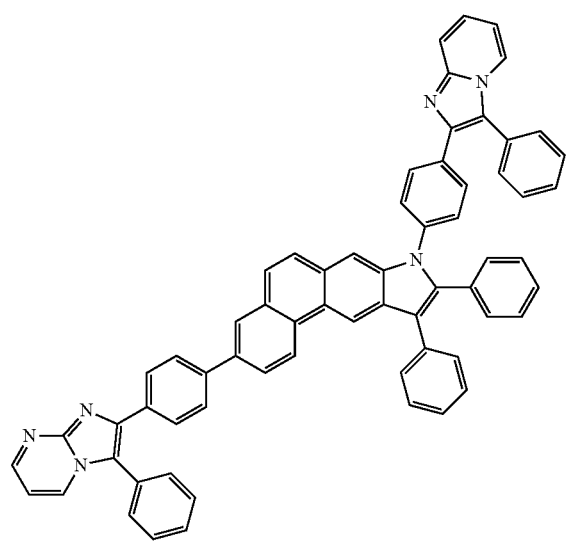
34
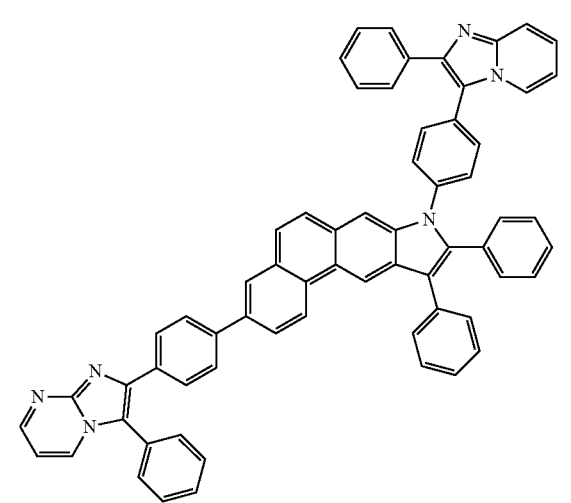
35
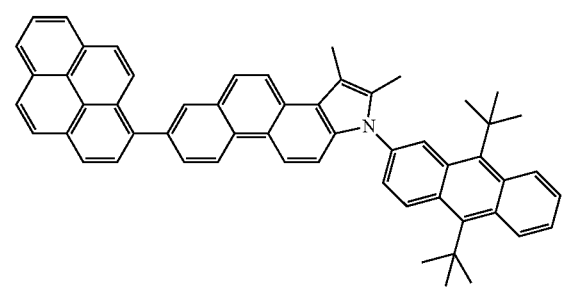
36
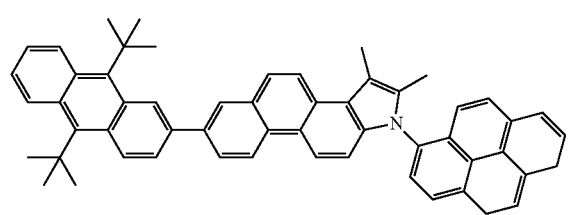
37
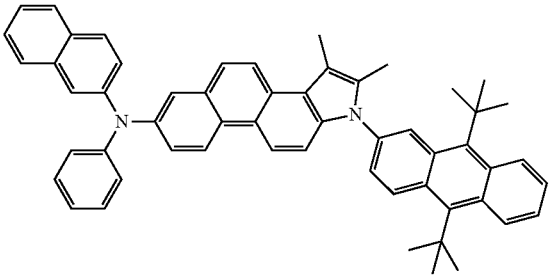
38
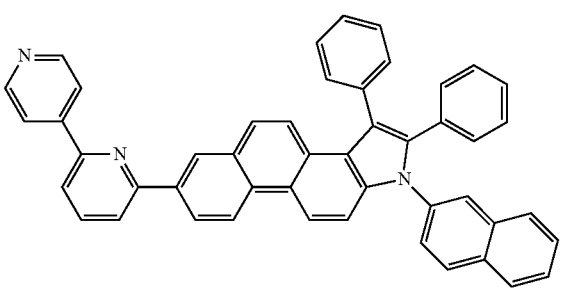
39
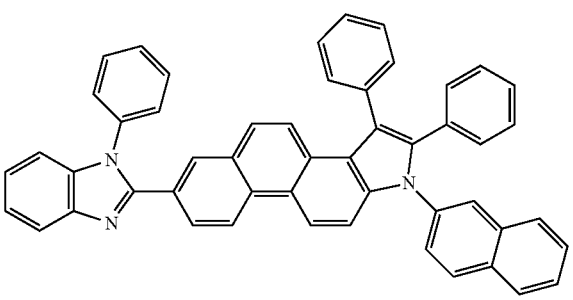
40
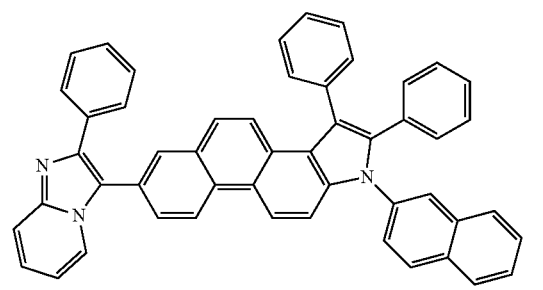
41
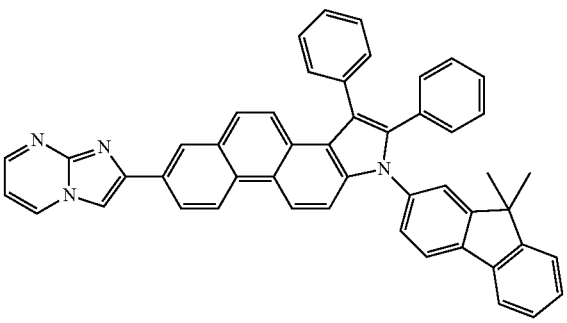

42
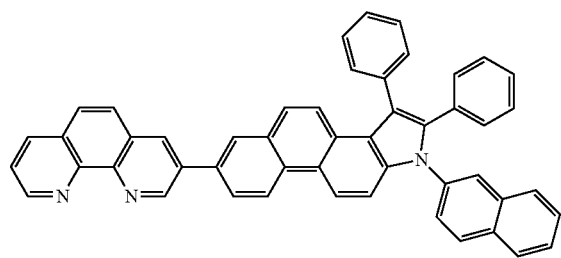
43
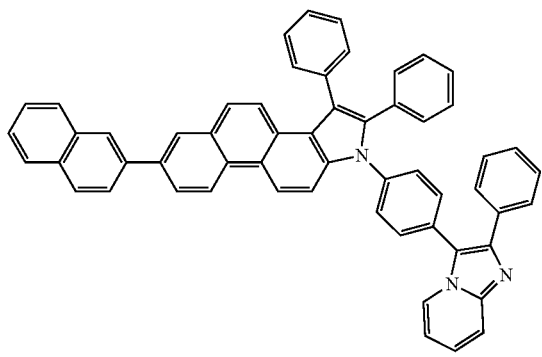
44
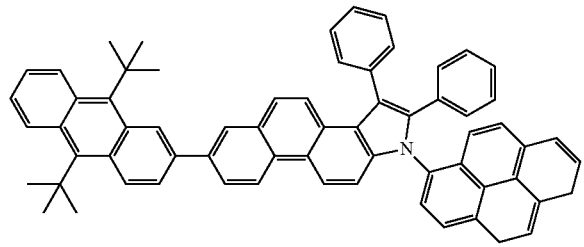
45
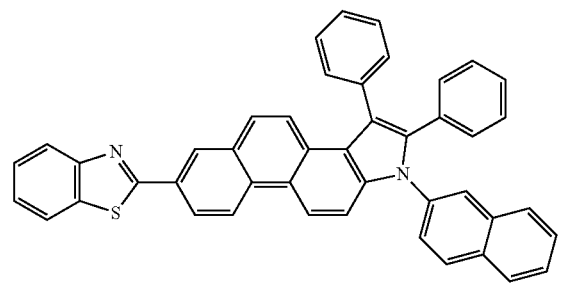
46
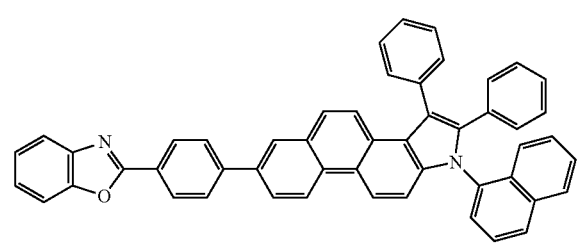
47
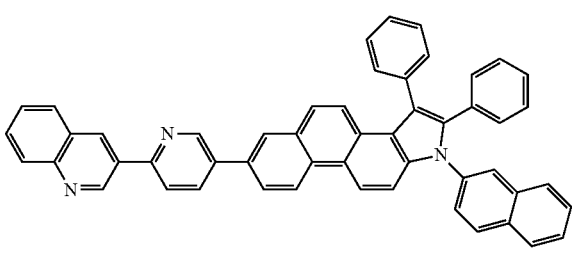
48
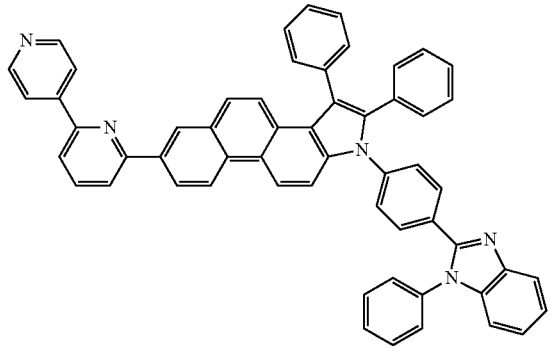
49
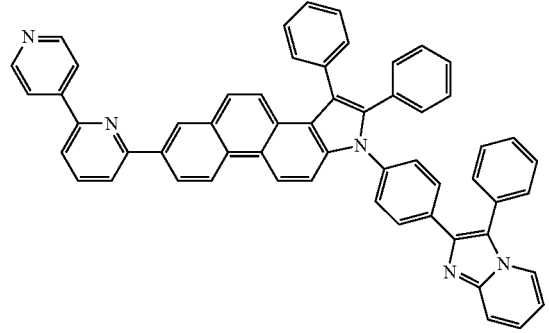
50
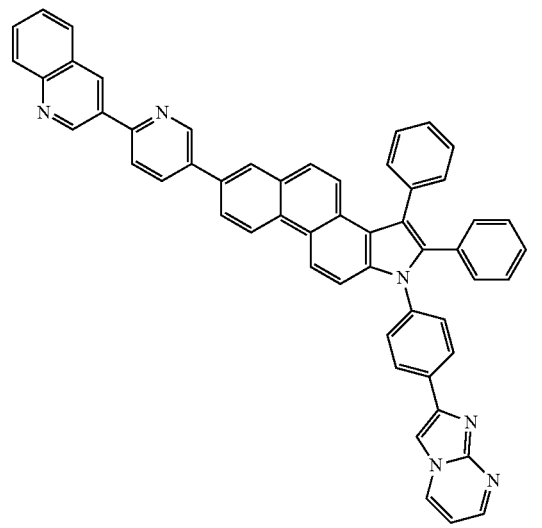

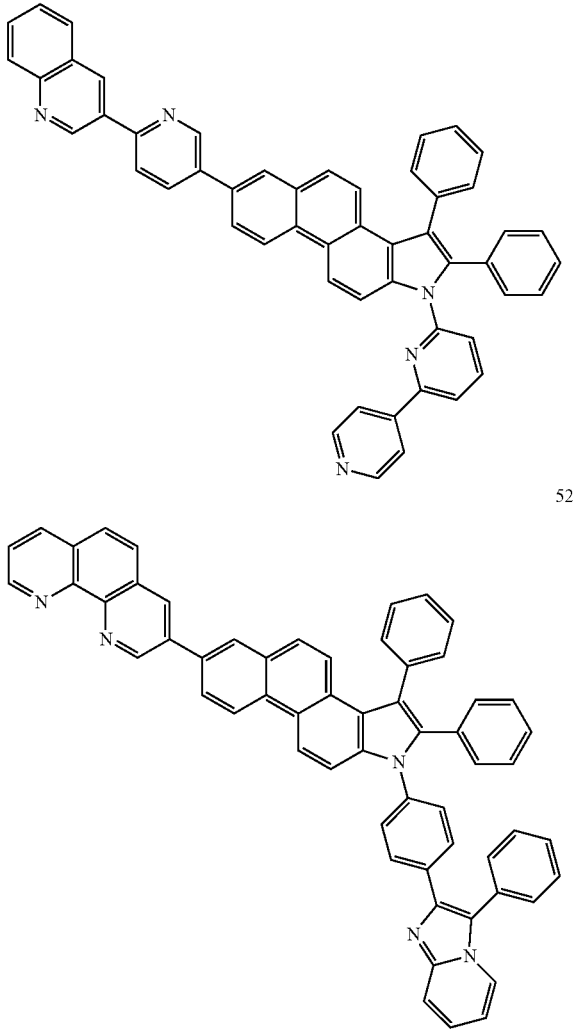

An organic light-emitting device according to an embodiment of the present invention includes a first electrode, a second electrode, and an organic layer between the first electrode and the second electrode, wherein the organic layer includes the heterocylic compound of Formula 1 or Formula 2 described above.

The organic layer including the heterocyclic compound of Formula 1 or Formula 2 may be an electron injection layer, a hole transport layer, or a single layer having both electron injection and electron transport capabilities. Alternatively, the organic layer including the heterocyclic compound of Formula 1 or Formula 2 may be an emission layer. When the organic layer including the heterocyclic compound of Formula 1 or Formula 2 is an emission layer, the heterocyclic compound of Formula 1 or Formula 2 may be used as a fluorescent host, a phosphorescent host, or a fluorescent dopant.

In the organic light-emitting device according to embodiments of the present invention, when the emission layer, the hole injection layer or the hole transport layer includes the heterocyclic compound of Formula 1 or Formula 2, the emission layer may include an anthracene compound, an arylamine compound or a styryl compound. The anthracene compound, the arylamine compound or the styryl compound may be unsubstituted or substituted with a substituent such as those described above with respect to the unsubstituted $C_1$-$C_{50}$ alkyl group.

In the organic light-emitting device according to embodiments of the present invention, when the hole injection layer or the hole transport layer includes the heterocyclic compound of Formula 1 or Formula 2, a red emission layer, a green emission layer, a blue emission layer, or a white emission layer may include a fluorescent compound.

The first electrode may be an anode, and the second electrode may be a cathode, but the reverse is also possible.

In the organic light-emitting described above, the organic layer may further include at least one layer selected from a hole injection layer, a hole transport layer, an electron blocking layer, an emission layer, a hole blocking layer, an electron transport layer and an electron injection layer. If desired, the respective layers described above may have a double-layer structure.

For example, the organic light-emitting device according to embodiments of the present invention may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. Alternatively, the organic light-emitting device may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure.

The organic light emitting device according to embodiments of the present invention may be a top-emission type organic light-emitting device or a bottom-emission type organic light-emitting device.

Hereinafter, a method of manufacturing an organic light-emitting device according to embodiments of the present invention will be described with reference to FIG. 1. FIG. 1 illustrates the structure of an organic light-emitting device according to embodiments of the present invention. Referring to FIG. 1, the organic light-emitting device includes a substrate, a first electrode (anode), a hole injection layer (HIL), a hole transport layer (HTL), an emission layer (EML), an electron transport layer (ETL), an electron injection layer (EIL), and a second electrode (cathode).

First, a first electrode material having a high work function may be deposited or sputtered on a substrate to form a first electrode. The first electrode may be an anode or a cathode. The substrate may be any substrate commonly used in organic light-emitting devices, and may be, for example, a glass substrate or a transparent plastic substrate having good mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

Next, the HIL may be formed on the first electrode by various methods, for example, by vacuum deposition, spin coating, casting, Langmuir-Blodgett (LB) deposition, or the like. When the HIL is formed using vacuum deposition, the deposition conditions may vary according to the compound used to form the HIL, and the desired structural and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, the coating conditions may vary according to the compound used to form the HIL, and the structural and thermal properties of the HIL to be formed. For example, the coating conditions may include a coating speed of about 2000 rpm to about 5000 rpm, and a thermal treatment temperature of about 80° C. to about 200° C., wherein the thermal treatment removes the solvent after the coating.

A HIL material may include any known HIL material. Nonlimiting examples of HIL materials include phthalocyanine compounds such as copper phthalocyanine, 4,4',4"-tris(3-methylphenylphenylamino)triphenylamine (m-MTDATA), N,N'-di(1-naphthyl)-N,N'-diphenylbenzidine) (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and (polyaniline)/poly(4-styrenesulfonate) (PANI/PSS).

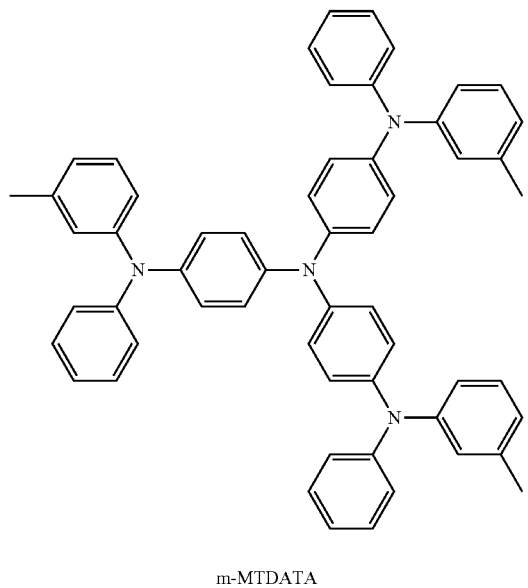

m-MTDATA

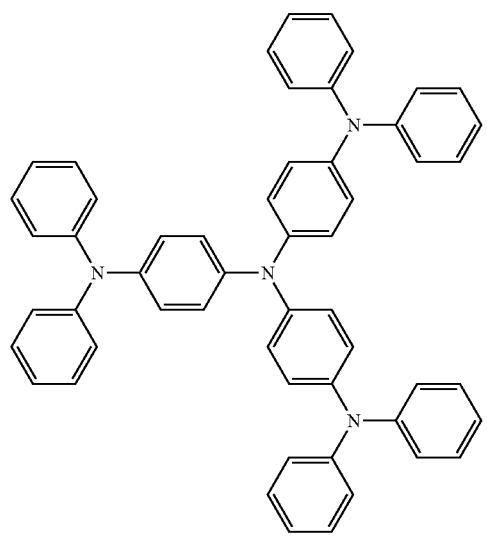

TDATA

-continued

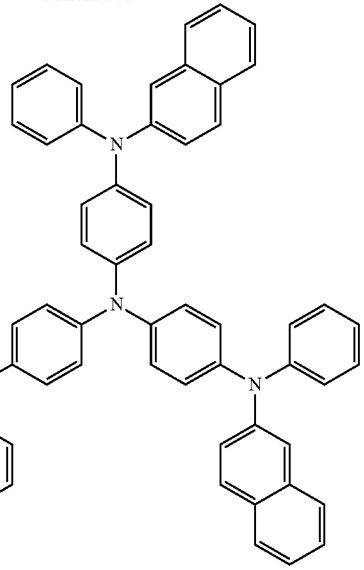

2-TNATA

The HIL may have a thickness of about 100 Å to about 10000 Å. In some embodiments, for example, the HIL has a thickness of about 100 Å to about 1000 Å. When the HIL has a thickness within these ranges, the HIL has good hole injection characteristics without increasing driving voltage.

Next, the HTL may be formed on the HIL by various methods, for example by vacuum deposition, spin coating, casting, LB deposition, or the like. When the HTL is formed by vacuum deposition or spin coating, the deposition or coating conditions may be similar to those used to form the HIL, although the deposition or coating conditions may vary according to the material used to form the HTL.

The HTL material may include a known HTL material. Nonlimiting examples of the HTL material may include carbazole derivatives such as N-phenylcarbazole or polyvinylcarbazole, and amine derivatives having an aromatic condensed ring, such as NPB, and N,N'-bis(3-methylphenyl)-N,N'-diphenyl-[1,1-biphenyl]-4,4'-diamine (TPD). Among these materials, TCTA not only transport holes but also inhibits excitons from being diffused from the EML.

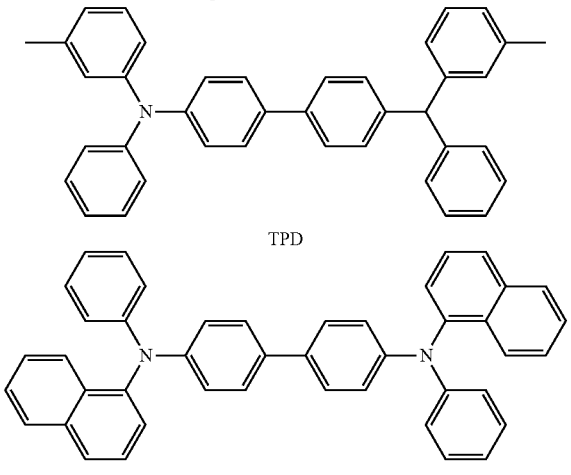

TPD

NPB

The HTL may have a thickness of about 50 Å to about 1000 Å. In some embodiments, for example, the HTL has a thickness of about 100 Å to about 600 Å. When the HTL has a thickness within these ranges, the HTL has good hole transport characteristics without substantially increasing driving voltage.

Next, the EML may be formed on the HTL by various methods, for example, by vacuum deposition, spin coating, casting, LB deposition, or the like. When the EML is formed by vacuum deposition or spin coating, the deposition or coating conditions may be similar to those used to form the HIL, although the deposition and coating conditions may vary according to the material used to form the EML.

The EML may include the heterocyclic compound of Formula 1 or Formula 2 described above. In particular, the heterocyclic compound of Formula 1 or Formula 2 may be used as a host or a dopant. The EML may include a variety of known light-emitting materials, in addition to the heterocyclic compound of Formula 1 or Formula 2. Alternatively, the EML may also be formed using known hosts and dopants. The dopant used to form the EML may include either a fluorescent dopant or a phosphorescent dopant, each of which may be a known material.

Nonlimiting examples of the host include $Alq_3$, CPB (4,4'-N,N'-dicarbazole-biphenyl), 9,10-di(naphthalene-2-yl)anthracene (ADN), and distyrylarylene (DSA).

Nonlimiting examples of red dopants include platinum(II) octaethylporphyrin (PtOEP), $Ir(piq)_3$, $Btp_2Ir(acac)$, and DCJTB.

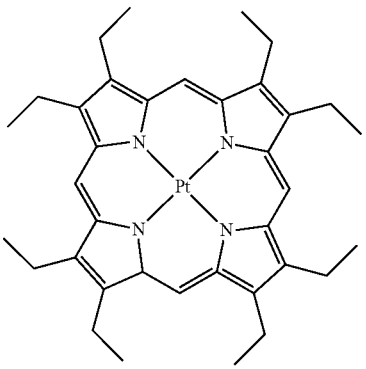

PtOEP

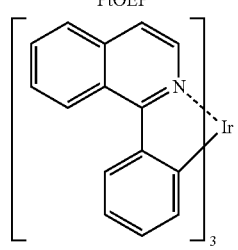

$Ir(piq)_3$

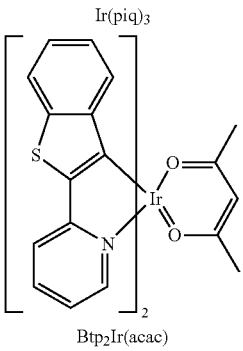

$Btp_2Ir(acac)$

Nonlimiting examples of green dopants include $Ir(ppy)_3$ (where "ppy" denotes phenylpyridine), $Ir(ppy)_2(acac)$, $Ir(mpyp)_3$, and C545T.

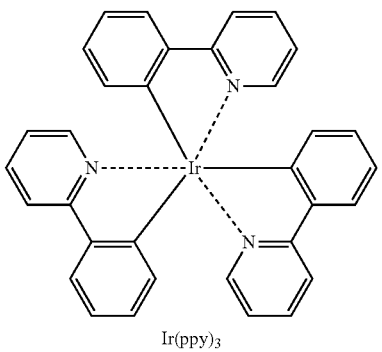

$Ir(ppy)_3$

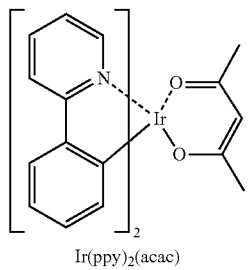

$Ir(ppy)_2(acac)$

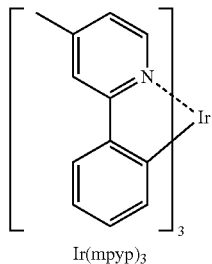

$Ir(mpyp)_3$

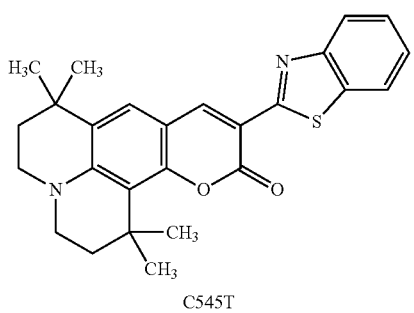

C545T

Nonlimiting examples of blue dopants include $F_2Irpic$, $(F_2ppy)_2Ir(tmd)$, $Ir(dfppz)_3$, ter-fluorene, 4,4'-bis(4-diphenylaminostyryl)biphenyl (DPAVBi), and 2,5,8,11-tetra-t-butyl perylene (TBPe).

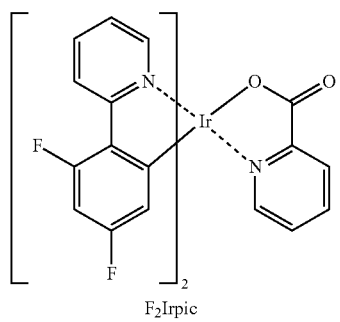

F₂Irpic

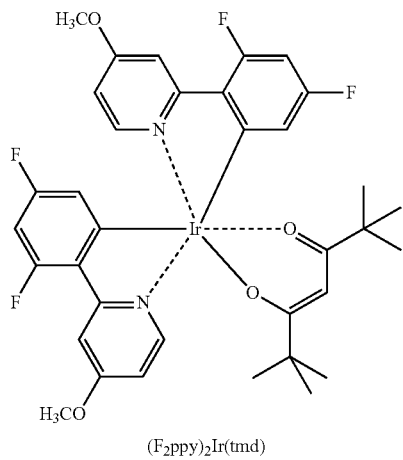

(F₂ppy)₂Ir(tmd)

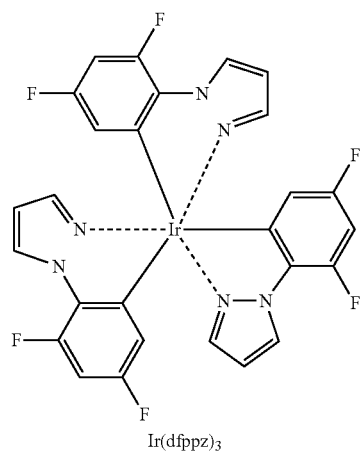

Ir(dfppz)₃

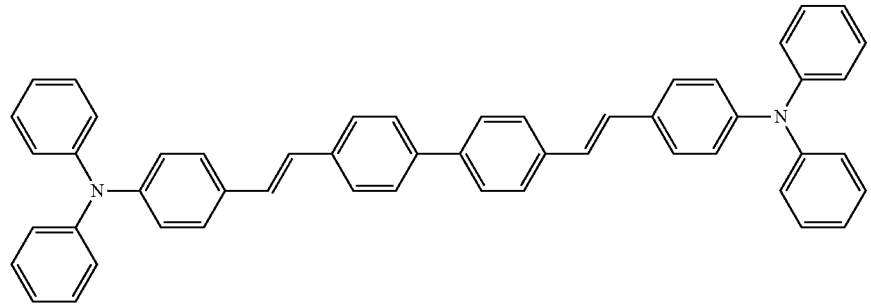

DPAVBi

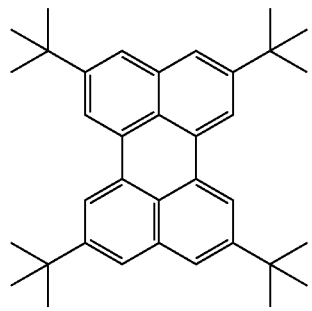

TBP

The amount of the dopant may be in the range of about 0.1 to about 20 parts by weight based on 100 parts by weight of the EML material (total weight of the host and dopant). In some embodiments, for example, the amount of the dopant is about 0.5 to about 12 parts by weight based on 100 parts by weight of the EML material (total weight of the host and dopant). When the amount of the dopant is within these ranges, concentration quenching may be substantially prevented.

The EML may have a thickness of about 100 Å to about 1000 Å. In some embodiment, for example, the EML has a thickness of about 200 Å to about 600 Å. When the EML has a thickness within these ranges, the EML has good light-emitting characteristics without substantially increasing driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form a HBL, without limitation. Nonlimiting examples of HBL materials include oxadiazole derivatives, triazole derivatives, phenanthroline derivatives, Balq, and BCP.

The HBL may have a thickness of about 50 Å to about 1000 Å. In some embodiments, for example, the HBL has a thickness of about 100 Å to about 300 Å. When the thickness of the HBL is within these ranges, the HBL has good hole blocking capability without substantially increasing driving voltage.

Next, the ETL is formed on the EML (or HBL) by various methods, for example, by vacuum deposition, spin coating, casting, or the like. When the ETL is formed by vacuum deposition or spin coating, the deposition or coating conditions may be similar to those used to form the HIL, although the deposition and coating conditions may vary according to the material used to form the ETL.

The ETL material may include the heterocyclic compound of Formula 1 or Formula 2 described above. Alternatively, the ETL may be formed of any material known in the art. Nonlimiting examples of ETL materials include quinoline derivatives, such as tris(8-quinolinolate)aluminum ($Alq_3$), TAZ, or Balq.

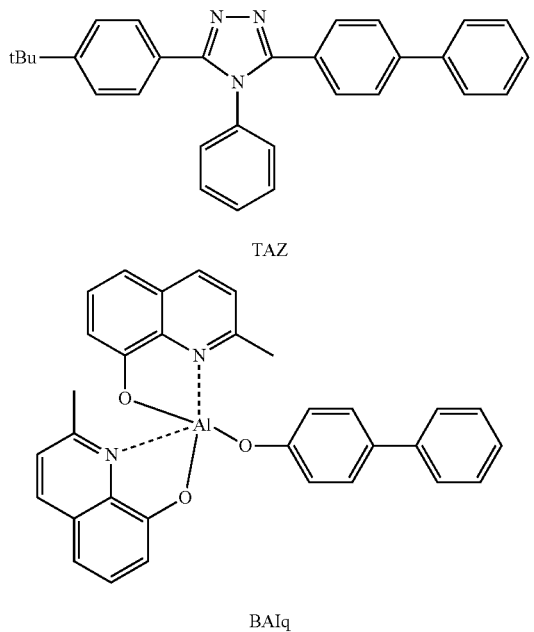

TAZ

BAlq

The ETL may have a thickness of about 100 Å to about 1000 Å. In some embodiment, for example, the ETL has a thickness of about 100 Å to about 500 Å. When the thickness of the ETL is within these ranges, the ETL has good electron transporting ability without substantially increasing driving voltage.

In addition, the EIL, which facilitates injection of electrons from the cathode, may be formed on the ETL. The EIL material may include the heterocyclic compound of Formula 1 or Formula 2 described above. Alternatively, known EIL materials, such as LiF, NaCl, CsF, $Li_2O$, or BaO, may be used to form the EIL. The deposition or coating conditions may be similar to those used to form the HIL, although the deposition and coating conditions may vary according to the material used to form the EIL.

The EIL may have a thickness of about 1 Å to about 100 Å. In some embodiments, for example, the EIL has a thickness of about 5 Å to about 90 Å. When the EIL has a thickness within these ranges, the EIL has good electron injection characteristics without substantially increasing driving voltage.

Finally, the second electrode may be formed on the EIL by, for example, vacuum deposition, sputtering, or the like. The second electrode may be a cathode or an anode. A material for forming the second electrode may be a metal, an alloy, or an electrically conductive compound, or a combination thereof, each of which has a low work function. Nonlimiting examples of such materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used as the second electrode.

The organic light-emitting device according to embodiments of the present invention may be used in various types of flat panel display devices, such as passive matrix organic light-emitting display devices or active matrix organic light-emitting display devices. In particular, when the organic light-emitting device is used in an active matrix organic light-emitting display device including a thin-film transistor, the first electrode on the substrate functions as a pixel electrode, and is electrically connected to a source electrode or a drain electrode of the thin-film transistor. Moreover, the organic light-emitting device may also be used in flat panel display devices having double-sided screens.

According to embodiments of the present invention, at least one layer of the organic light-emitting device may be formed of the heterocyclic compound of Formula 1 or Formula 2 and may be applied by a deposition method or a wet method of coating a solution of the heterocylic compound of Formula 1 or Formula 2.

The following Examples are presented for illustrative purposes only, and do not limit the scope of the present invention.

EXAMPLE

Synthesis Example

Synthesis of Compound 10

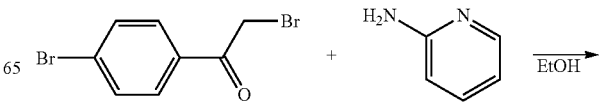

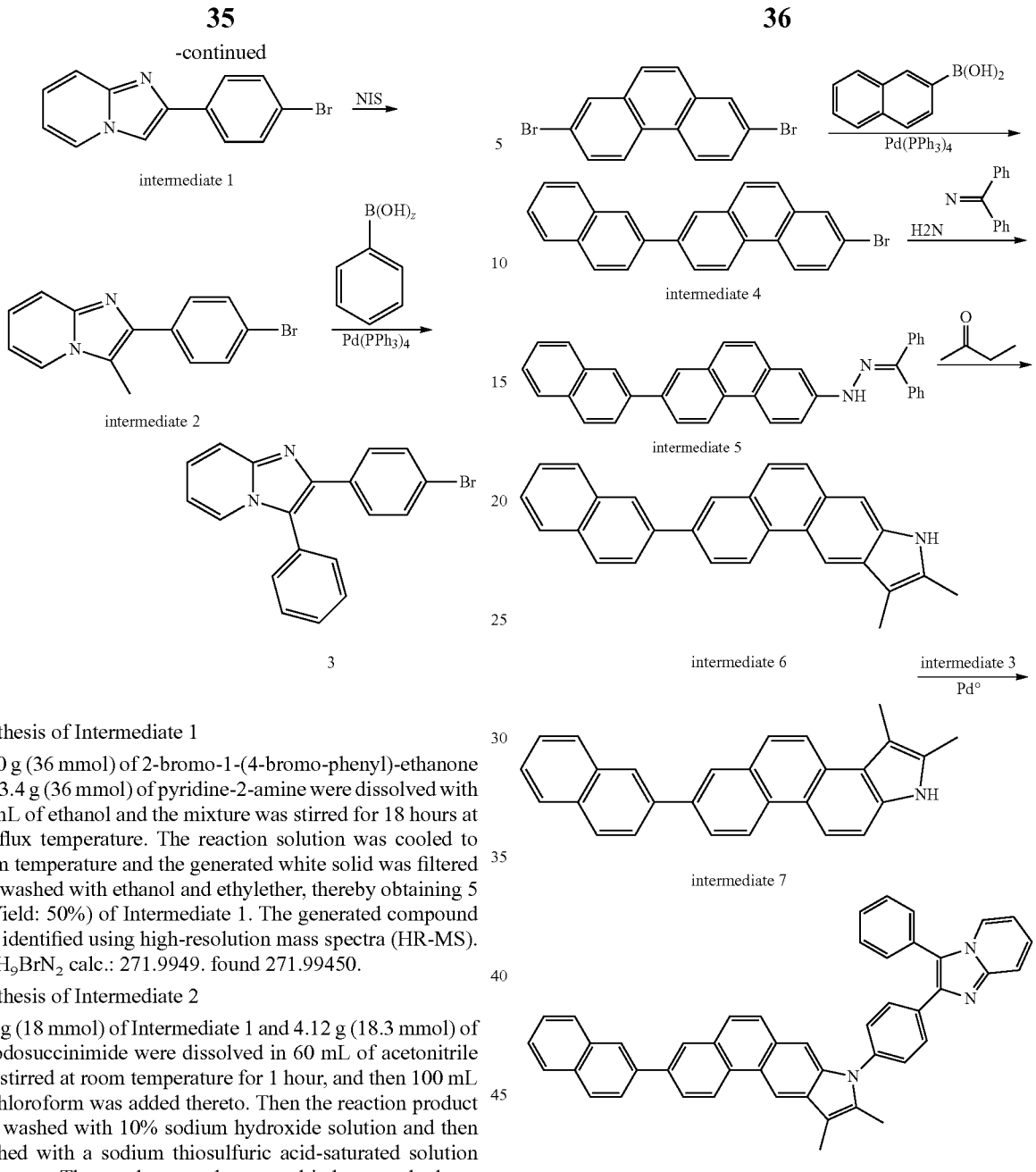

Synthesis of Intermediate 1

10 g (36 mmol) of 2-bromo-1-(4-bromo-phenyl)-ethanone and 3.4 g (36 mmol) of pyridine-2-amine were dissolved with 50 mL of ethanol and the mixture was stirred for 18 hours at a reflux temperature. The reaction solution was cooled to room temperature and the generated white solid was filtered and washed with ethanol and ethylether, thereby obtaining 5 g (Yield: 50%) of Intermediate 1. The generated compound was identified using high-resolution mass spectra (HR-MS). $C_{13}H_9BrN_2$ calc.: 271.9949. found 271.99450.

Synthesis of Intermediate 2

5 g (18 mmol) of Intermediate 1 and 4.12 g (18.3 mmol) of N-iodosuccinimide were dissolved in 60 mL of acetonitrile and stirred at room temperature for 1 hour, and then 100 mL of chloroform was added thereto. Then the reaction product was washed with 10% sodium hydroxide solution and then washed with a sodium thiosulfuric acid-saturated solution and water. The resultant product was dried over anhydrous magnesium sulfate and filtered to remove the solvent, thereby obtaining a solid product. The solid product was washed with methanol and filtered to obtain 5.8 g (Yield: 81%) of Intermediate 2. The generated compound was identified using HR-MS. $C_{13}H_8BrIN_2$ calc.: 397.8916. found 397.8917.

Synthesis of Intermediate 3

5.8 g (14.5 mmol) of Intermediate 2, 1.8 g (14.7 mmol) of phenylboronic acid, 335 mg (0.2 mmol) of $Pd(PPh_3)_4$, and 10 g (72 mmol) of $K_2CO_3$ were dissolved in 100 mL of a THF/$H_2O$(2:1) mixed solution, and stirred at a temperature of 80° C. for 18 hours. The reaction solution was extracted three times with 100 ml of diethylether. An organic layer was collected and dried using magnesium sulfate to evaporate the solvent. The residue was separated and purified by silica gel column chromatography to obtain 2.9 g (Yield: 57%) of Intermediate 3. The generated compound was identified using HR-MS. $C_{19}H_{13}BrN_2$ calc.: 348.0262. found 348.0265.

Synthesis of Intermediate 4

6.8 g (30 mmol) of 2,7-dibromophenanthrene, 3.4 g (20 mmol) of 2-naphthylboric acid, 1.1 g (1 mmol) of $Pd(PPh_3)_4$, and 13.8 g (100 mmol) of $K_2CO_3$ were dissolved in 120 mL of a THF/$H_2O$(2:1) mixed solution and stirred at a temperature of 80° C. for 5 hours. The reaction solution was extracted three times with 100 ml of diethylether. An organic layer was collected and dried using magnesium sulfate to evaporate the solvent. The residue was separated and purified by silica gel column chromatography to obtain 4.67 g of Intermediate 4 (Yield: 61%). The generated compound was identified using HR-MS. $C_{24}H_{15}Br$ calc.: 382.0357. found 382.0359.

Synthesis of Intermediate 5

3.83 g (10 mmol) of Intermediate 4, 2 g (10.1 mmol) of benzophenone hydrazone, 1.44 g (15 mmol) of t-BuONa, 112 mg (0.5 mmol) of $Pd(OAc)_2$, and 238 mg (0.5 mmol) of 2-dicyclohexylphosphino-2',4',6'-triisopropylbiphenyl were dissolved in 50 mL of toluene and stirred at a temperature of 90° C. for 3 hours. The reaction solution was cooled to room temperature and then distilled water was added thereto and extracted twice with 50 mL of diethylether and once with 50 mL of dichloromethane. An organic layer was collected and dried using magnesium sulfate to evaporate the solvent. The residue was separated and purified by silica gel column chromatography to obtain 4.24 g (Yield: 85%) of Intermediate 5. The generated compound was identified using HR-MS. $C_{37}H_{26}N_2$ calc.: 498.2096. found 498.2099.

Synthesis of Intermediate 6

15 mL of methylethylketone and 10 mL of toluene were added to a mixture including 1.5 g (3.0 mmol) of Intermediate 5 and 1.14 g (6.0 mmol) of p-toluenesulfonic acid monohydrate and then the resultant mixture was stirred at a temperature of 110° C. for 24 hours. During this reaction, Intermediate 6 and Intermediate 7, which are isomers of each other, were formed. In this experiment, only one type of isomer was dominantly formed and the other isomer was formed in a very small amount. The reaction product was cooled to room temperature and distilled water was added thereto, and then the resultant reaction product was extracted twice with 25 mL of diethylether and twice with 25 mL of dichloromethane. An organic layer was collected and dried using magnesium sulfate to evaporate the solvent. The residue was separated and purified by silica gel column chromatography to obtain 1.4 g (Yield: 69%) of Intermediate 6 and 100 mg (Yield: 8.9%) of Intermediate 7. The generated compounds were identified using HR-MS. In this experiment, only Intermediate 6, which is a major product, was used. Intermediate 6: $C_{28}H_{21}N$ calc.: 371.1674. found 371.1677. Intermediate 7: $C_{28}H_{21}N$ calc.: 371.1674. found 371.1678.

Synthesis of Compound 10

3.71 g (10 mmol) of Intermediate 6, 4.19 g (12 mmol) of Intermediate 3, 2.9 g (30 mmol) of t-BuONa, 366 mg (0.4 mmol) of $Pd_2(dba)_3$, and 80 mg (0.4 mmol) of $P(t-Bu)_3$ were dissolved in 60 mL of toluene, and then the mixture was stirred at a temperature of 90° C. for 3 hours. After the reaction was completed, the reaction product was cooled to room temperature and extracted three times with distilled water and 50 ml of diethylether. An organic layer was collected and dried using magnesium sulfate to evaporate the solvent. The residue was separated and purified by silica gel column chromatography to obtain 4.67 g (Yield: 73%) of Compound 10. The generated compound was identified using HR-MS. $C_{47}H_{33}N_3$ calc.: 639.2674. found 639.2678. $^1H$ NMR (CDCl$_3$, 400 MHz) δ (ppm) 8.89 (s, 1H), 8.53 (d, 1H), 8.40-8.36 (m, 3H), 8.13 (dd, 1H). 8.07 (d, 1H), 7.98 (d, 1H), 7.96-7.82 (m, 6H), 7.61-7.53 (m, 2H), 7.48-7.36 (m, 6H), 7.33-7.28 (m, 2H), 7.14 (dt, 1H), 6.96 (d, 2H), 2.45 (s, 3H), 2.42 (s, 3H)

Synthesis Example

Synthesis of Compound 17

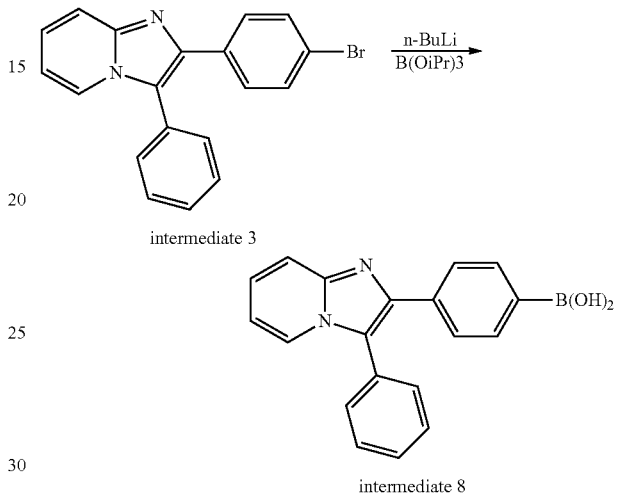

Synthesis of Intermediate 8

Under nitrogen gas, 6.98 g (20 mmol) of Intermediate 3 was dissolved in 80 mL of THF and the temperature was dropped to −78° C. At the temperature of −78° C., 8.8 mL (22 mmol, 2.5M in hexane) of n-butyllithium was slowly dropwise added thereto and then the mixture was stirred for one hour. Then, 9.2 mL (60 mmol) of B(OiPr)$_3$ was added thereto and the temperature was increased to room temperature and then the resultant mixture was stirred for three hours. When the reaction was completed, 10% HCl aqueous solution was added thereto. The reaction solution was extracted three times with 100 mL of diethylether. An organic layer was collected and dried using magnesium sulfate to evaporate the solvent. The residue was re-crystallized with dichloromethane and normal hexane to obtain 4.52 g (Yield: 72%) of Intermediate 8. The generated compound was identified using HR-MS. $C_{19}H_{15}BN_2O_2$ calc.: 314.1227. found 314.1224.

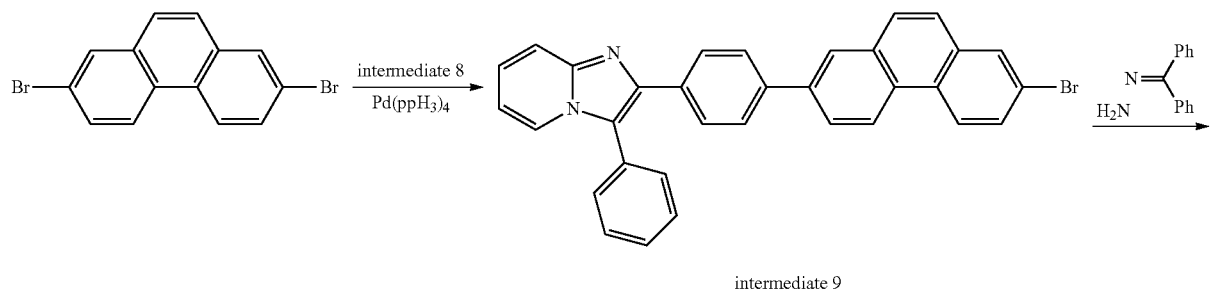

-continued

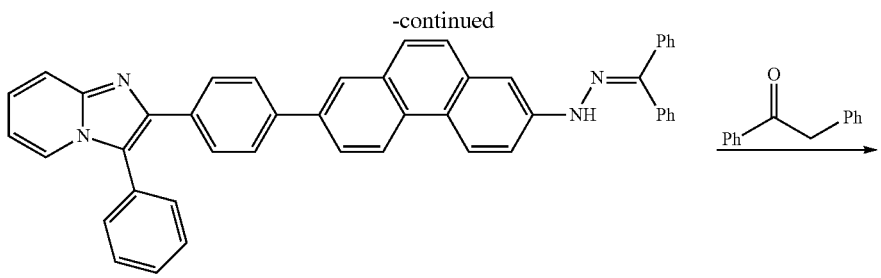

Intermediate 10

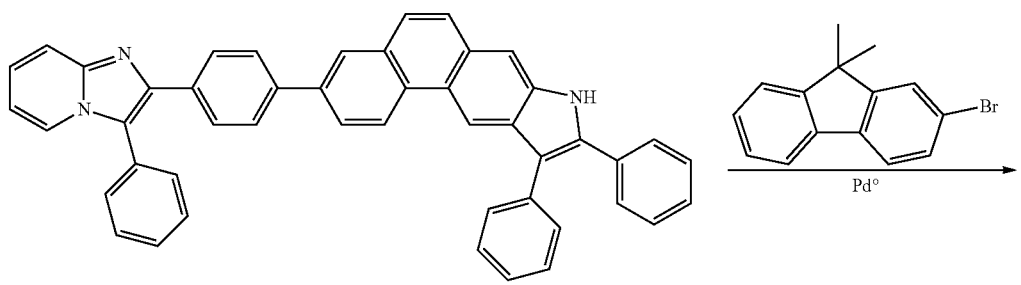

Intermediate 11

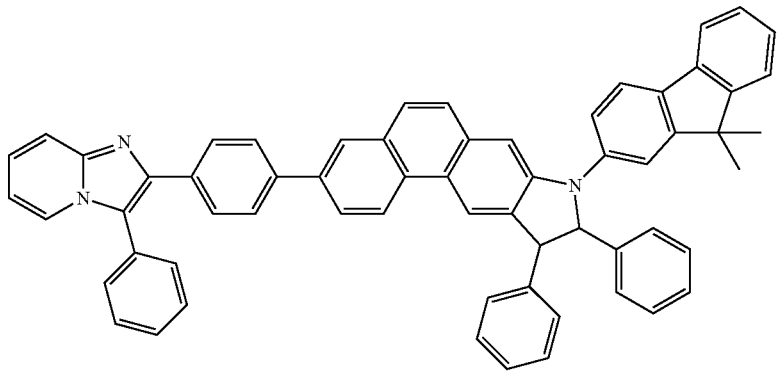

17

Synthesis of Intermediate 9

6.62 g (Yield: 63%) of Intermediate 9 was obtained using the same method used to synthesize Intermediate 4, except that Intermediate 8 was used instead of 2-naphthylboric acid. The generated compound was identified using HR-MS. $C_{33}H_{21}BrN_2$ calc.: 524.0888. found 524.0885.

Synthesis of Intermediate 10

5.7 g (Yield: 89%) of Intermediate 10 was obtained using the same method used to synthesize Intermediate 5, except that Intermediate 9 was used instead of Intermediate 4. The generated compound was identified using HR-MS. $C_{46}H_{32}N_4$ calc.: 640.2627. found 640.2630.

Synthesis of Intermediate 11

40 mL of ethanol and 20 mL of toluene were added to a mixture including 6.4 g (10 mmol) of Intermediate 10, 3.44 g (20 mmol) of p-toluenesulfonic acid monohydrate, and 3.92 g (20 mmol) of benzylphenylketone and then stirred at a temperature of 110° C. for 24 hours. The reaction solution was cooled to room temperature and distilled water was added thereto. The resultant reaction solution was extracted twice with 50 mL of diethylether and twice with 50 mL of dichloromethane. An organic layer was collected and dried using magnesium sulfate to evaporate the solvent. The residue was separated and purified by silica gel column chromatography to obtain 4.65 g (Yield: 73%) of Intermediate 11 as a major product. The generated compound was identified using HR-MS. $C_{47}H_{31}N_3$ calc.: 637.2518. found 637.2521.

Synthesis of Compound 17

6.55 g (Yield: 79%) of Compound 17 was obtained using the same method used to synthesize Compound 10, except that Intermediate 11 was used instead of Intermediate 6 and 2-bromo-9,9'-dimethylfluorene was used instead of Intermediate 3. The generated compound was identified using HR-MS. $C_{62}H_{43}N_3$ calc.: 829.3457. found 829.3456. $^1$H NMR (CDCl$_3$, 400 MHz) δ (ppm) 9.1 (s, 1H), 8.63 (d, 2H), 8.49 (d, 1H), 8.21 (d, 1H), 8.12-7.89 (m, 6H), 7.76 (d, 1H), 7.73-7.37 (m, 16H), 7.36-7.24 (m, 3H), 7.22 (d, 1H), 7.18 (dt, 1H), 7.12 (dt, 1H), 7.06-6.93 (m, 2H), 6.87 (dd, 1H), 1.93 (s, 6H)

Synthesis Example
Synthesis of Compound 27
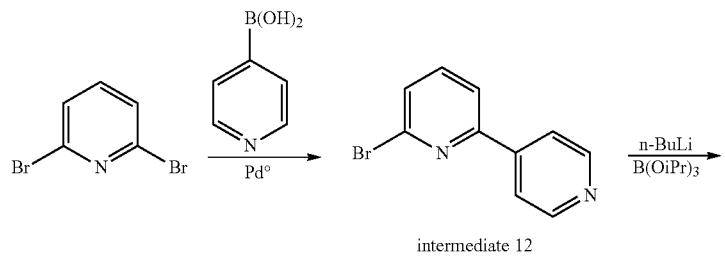
intermediate 12
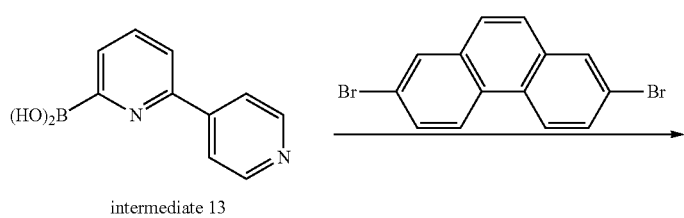
intermediate 13
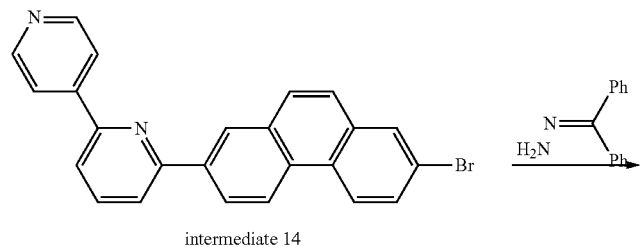
intermediate 14
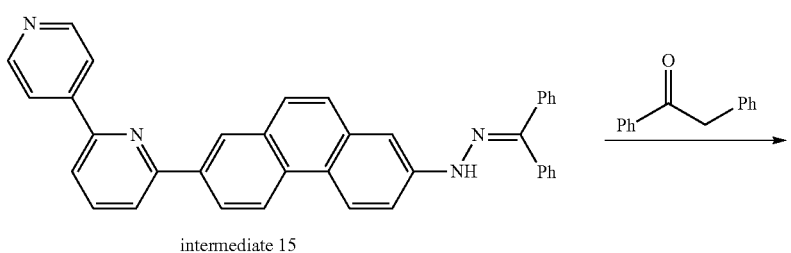
intermediate 15
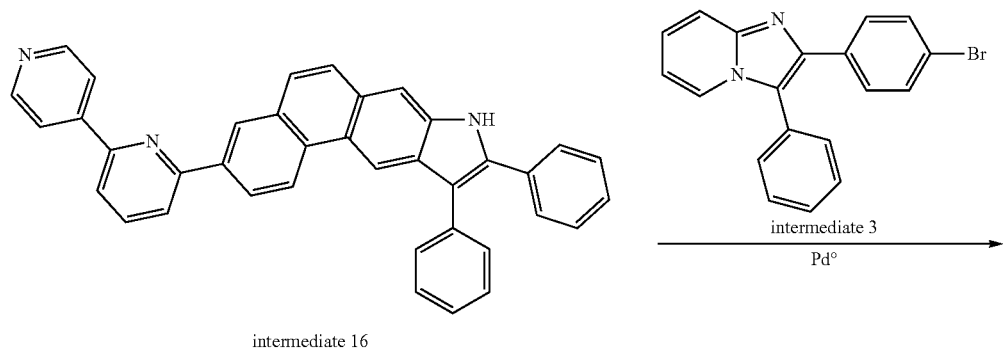
intermediate 16

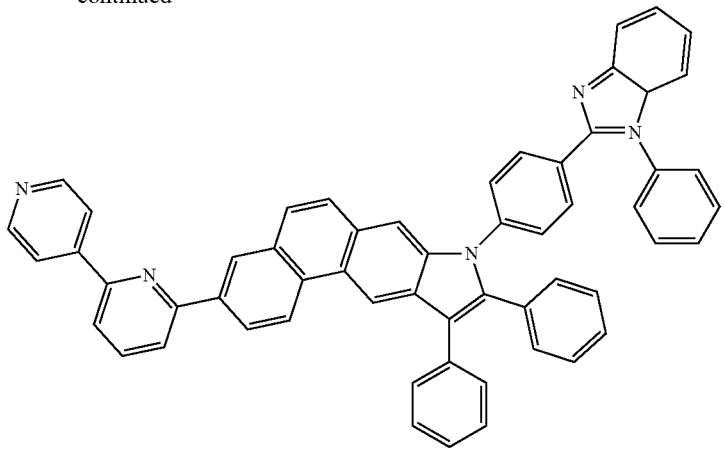

compound 27

Synthesis of Intermediate 12

6.16 g (26 mmol) of 2,5-dibromopyridine, 2.46 g (20 mmol) of 4-pyridylboronic acid, 1.16 g (1 mmol) of Pd(PPh$_3$)$_4$, and 11.1 g (80 mmol) of K$_2$CO$_3$ were dissolved in 100 mL of a THF/H$_2$O (2:1) mixed solution and stirred at a temperature of 80° C. for 5 hours. The reaction solution was extracted three times with 100 ml of diethylether. An organic layer was collected and dried using magnesium sulfate to evaporate the solvent. The residue was re-crystallized with dichloromethane and normal hexane to obtain 3.47 g (Yield: 72%) of Intermediate 12. The generated compound was identified using HR-MS. C$_{10}$H$_7$BrN$_2$ calc.: 233.9793. found 233.9795.

Synthesis of Intermediate 13

2.72 g (Yield: 68%) of Intermediate 13 was obtained using the same method used to synthesize Intermediate 8, except that Intermediate 12 was used instead of Intermediate 3. The generated compound was identified using HR-MS. C$_{10}$H$_9$BN$_2$O$_2$ calc.: 200.0757. found 200.0753.

Synthesis of Intermediate 14

2.67 g (Yield: 65%) of Intermediate 14 was obtained using the same method used to synthesize Intermediate 4, except that Intermediate 13 was used instead of 2-naphthylboronic acid. The generated compound was identified using HR-MS. C$_{24}$H$_{15}$BrN$_2$ calc.: 410.0419. found 410.0421.

Synthesis of Intermediate 15

5.7 g (Yield: 89%) of Intermediate 15 was obtained using the same method used to synthesize Intermediate 5, except that Intermediate 14 was used instead of Intermediate 4. The generated compound was identified using HR-MS. C$_{37}$H$_{26}$N$_4$ calc.: 526.2157. found 526.2161.

Synthesis of Intermediate 16

3.2 g (Yield: 62%) of Intermediate 16 was obtained using the same method used to synthesize Intermediate 11, except that Intermediate 15 was used instead of Intermediate 10. The generated compound was identified using HR-MS. C$_{38}$H$_{25}$N$_3$ calc.: 523.2048. found 523.2046.

Synthesis of Compound 27

5.78 g (Yield: 73%) of Compound 27 was obtained using the same method used to synthesize Compound 10, except that Intermediate 16 was used instead of Intermediate 6. The generated compound was identified using HR-MS. C$_{57}$H$_{37}$N$_5$ calc.: 791.3049. found 791.3052. $^1$H NMR (CDCl$_3$, 400 MHz) δ (ppm) 9.20 (s, 1H), 8.74 (s, 1H), 8.63-8.56 (m, 3H), 8.52 (s, 1H), 8.45 (d, 2H), 8.29 (t, 1H), 8.03 (dd, 2H), 7.90 (dd, 2H), 7.84 (d, 1H), 7.73 (d, 1H), 7.55 (dt, 3H), 7.53-7.39 (m, 12H), 7.34-7.23 (m, 4H), 7.15 (dt, 1H), 7.04 (d, 2H)

Synthesis Example

Synthesis of Compound 33

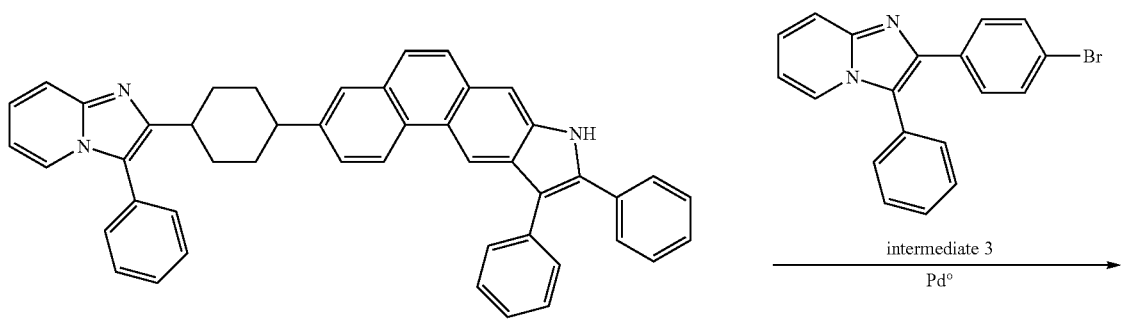

intermediate 11 intermediate 3
Pd°

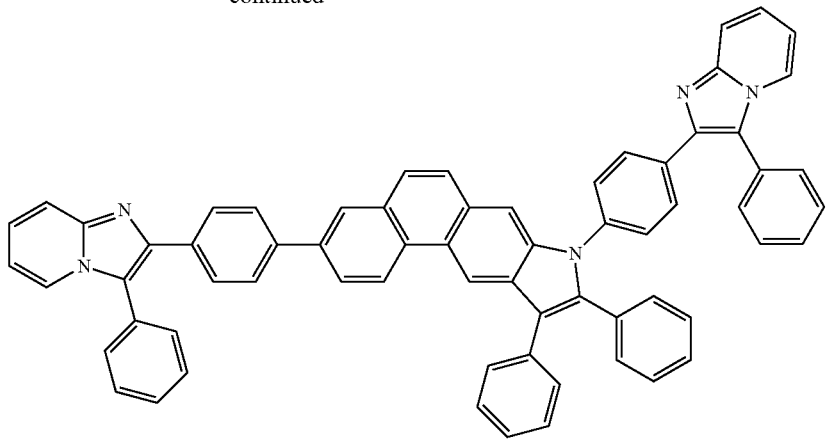
33
7.06 g (Yield: 78%) of Compound 33 was obtained using the same method used to synthesize Compound 17, except that Intermediate 3 was used instead of 2-bromo-9,9'-dimethylfluorene. The generated compound was identified using HR-MS. $C_{66}H_{43}N_5$ calc.: 905.3518. found 905.3516. $^1$H NMR (CDCl$_3$, 400 MHz) δ (ppm) 9.17 (s, 1H), 8.58-8.47 (m, 3H), 8.42 (dd, 1H), 8.35 (d, 1H), 8.13 (d, 2H), 8.01 (d, 1H), 7.96 (d, 2H), 7.90-7.82 (m, 5H), 7.71 (d, 2H), 7.56 (dd, 4H), 7.52-7.25 (m, 16H), 7.09 (tt, 1H), 7.01 (d, 2H), 6.97-6.86 (m, 2H)
Synthesis Example
Synthesis of Compound 42
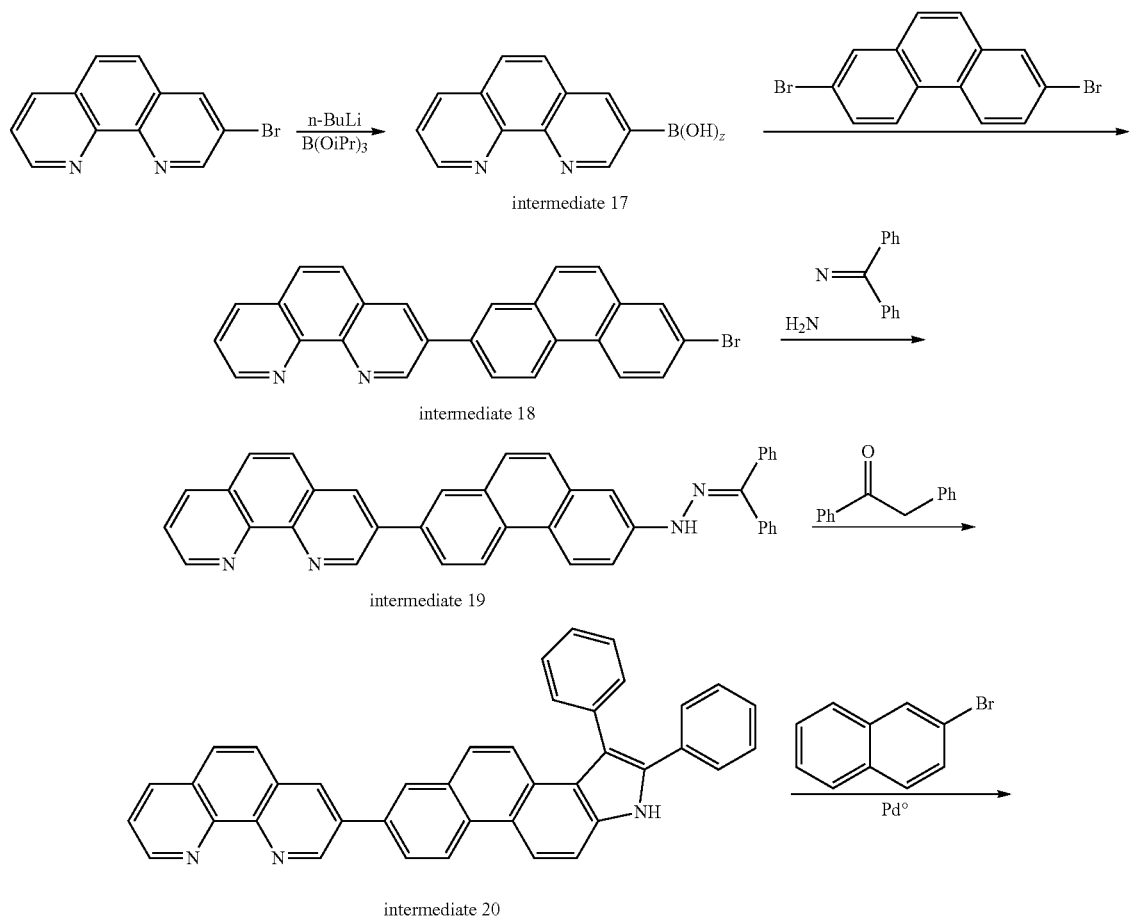

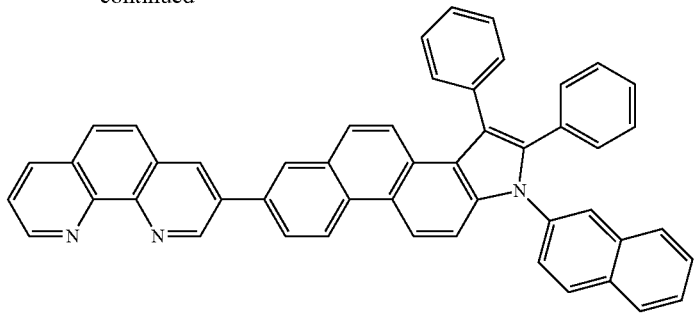

42

Synthesis of Intermediate 17

4.76 g (Yield: 79%) of Intermediate 17 was obtained using the same method used to synthesize Intermediate 8, except that 3-bromo-1,10-phenanthroline was used instead of Intermediate 3. The generated compound was identified using HR-MS. $C_{12}H_9BN_2O_2$ calc.: 224.0757. found 224.0755.

Synthesis of Intermediate 18

2.66 g (Yield: 61%) of Intermediate 18 was obtained using the same method used to synthesize Intermediate 4, except that Intermediate 17 was used instead of 2-naphthylboronic acid. The generated compound was identified using HR-MS. $C_{26}H_{15}BrN_2$ calc.: 434.0419. found 434.0417.

Synthesis of Intermediate 19

4.18 g (Yield: 76%) of Intermediate 19 was obtained using the same method used to synthesize Intermediate 5, except that Intermediate 18 was used instead of Intermediate 4. The generated compound was identified using HR-MS. $C_{39}H_{26}N_4$ calc.: 550.2157. found 550.2159.

Synthesis of Intermediate 20

2.46 g (Yield: 45%) of Intermediate 20 was obtained as a major product using the same method used to synthesize Intermediate 11, except that Intermediate 19 was used instead of Intermediate 10. The generated compound was identified using HR-MS. $C_{40}H_{25}N_3$ calc.: 547.2048. found 547.2049.

Synthesis of Compound 42

4.78 g (Yield: 71%) of Compound 42 was obtained using the same method used to synthesize Compound 10, except that Intermediate 20 was used instead of Intermediate 10. The generated compound was identified using HR-MS. $C_{50}H_{31}N_3$ calc.: 673.2518. found 673.2519. $^1$H NMR (CDCl$_3$, 400 MHz) δ (ppm) 8.84 (d, 1H), 8.79 (dd, 2H), 8.45 (d, 1H), 8.31 (d, 1H), 8.27 (d, 1H), 8.19 (d, 1H), 8.07 (dd, 1H), 7.90 (d, 1H), 7.83 (d, 2H), 7.76 (d, 1H), 7.73 (d, 1H), 7.69 (d, 1H), 7.67-7.62 (m, 2H), 7.51 (dd, 1H), 7.49-7.27 (m, 12H), 7.25-7.13 (m, 2H)

Example 1

An anode was prepared by cutting a Corning 15 Ωcm$^2$ (1200 Å) ITO glass substrate to a size of 50 mm×50 mm×0.7 mm, ultrasonically cleaning the glass substrate using isopropyl alcohol and pure water for 5 minutes each, and then irradiating with UV light for 30 minutes and exposing to ozone to clean. Then, the anode was mounted in a vacuum deposition apparatus.

First, 2-TNATA as a HIL material was vacuum-deposited on the glass substrate to form a HIL having a thickness of 600 Å. Then, 4,4'-bis[N-(1-naphthyl)-N-phenylamino]biphenyl (hereinafter referred to as NPB) as a HTL material was vacuum deposited on the HIL to form a HTL having a thickness of 300 Å.

Then, Compound 10 was deposited on the EML to form an ETL having a thickness of 300 Å. Then, LiF (a halogenated alkali metal) was deposited on the ETL to form an EIL having a thickness of 10 Å. Then, Al was deposited on the EIL to a thickness of 3000 Å (cathode), thereby forming a LiF/Al electrode. As a result, the manufacture of an organic light-emitting device was completed.

The organic light-emitting device had a driving voltage of 5.83 V at a current density of 50 mA/cm$^2$, a high emission brightness of 8,260 cd/m$^2$, color coordinates of (0.311, 0.643), and an emission efficiency of 16.52 cd/A.

Example 2

An organic light-emitting device was manufactured as in Example 1, except that Compound 17 was used instead of Compound 10 to form the ETL.

The organic light-emitting device had a driving voltage of 6.18 V at a current density of 50 mA/cm$^2$, a high emission brightness of 8,540 cd/m$^2$, color coordinates of (0.310, 0.644), and an emission efficiency of 17.08 cd/A.

Example 3

An organic light-emitting device was manufactured as in Example 1, except that Compound 27 was used instead of Compound 10 to form the ETL.

The organic light-emitting device had a driving voltage of 5.59 V at a current density of 50 mA/cm$^2$, a high emission brightness of 8,956 cd/m$^2$, color coordinates of (0.309, 0.643), and an emission efficiency of 17.91 cd/A.

Example 4

An organic light-emitting device was manufactured as in Example 1, except that Compound 33 was used instead of Compound 10 to form the ETL.

The organic light-emitting device had a driving voltage of 5.49 V at a current density of 50 mA/cm$^2$, a high emission brightness of 8,987 cd/m$^2$, color coordinates of (0.310, 0.644), and an emission efficiency of 17.97 cd/A.

Example 5

An organic light-emitting device was manufactured as in Example 1, except that Compound 42 was used instead of Compound 10 to form the ETL.

The organic light-emitting device had a driving voltage of 5.91 V at a current density of 50 mA/cm$^2$, a high emission brightness of 8,023 cd/m², color coordinates of (0.311, 0.643), and an emission efficiency of 16.04 cd/A.

Comparative Example 1

An organic light-emitting device was manufactured as in Example 1, except that Alq₃ was used instead of Compound 10 to form the ETL.

The organic light-emitting device had a driving voltage of 7.45 V at a current density of 50 mA/cm², a high emission brightness of 6,102 cd/m², color coordinates of (0.309, 0.642), and an emission efficiency of 12.2 cd/A.

The organic light-emitting devices manufactured using the heterocyclic compounds of Formula 1 or Formula 2 as an ETL material according to Examples 1 through 5 had a driving voltage that was lower by 1 V or greater than when Alq3 was used, and thus had higher efficiency and good I-V-L characteristics. In particular, lifetime characteristics were markedly improved by 100% or greater in the organic light-emitting devices according to Examples 1 through 5 compared with the organic light-emitting device according to Comparative Example 1. The results are shown in Table 1 below.

TABLE 1

| | ETL material | Driving voltage (V) | Current density (mA/cm²) | Brightness (cd/m²) | Efficiency (cd/A) | Color coordinate | Half-life span (hr @ 100 mA/cm²) |
|---|---|---|---|---|---|---|---|
| Example 1 | Compound 10 | 5.83 | 50 | 8260 | 16.52 | (0.311, 0.643) | 503 hr |
| Example 2 | Compound 17 | 6.18 | 50 | 8540 | 17.08 | (0.310, 0.644) | 548 hr |
| Example 3 | Compound 27 | 5.59 | 50 | 8956 | 17.91 | (0.309, 0.643) | 564 hr |
| Example 4 | Compound 33 | 5.49 | 50 | 8987 | 17.97 | (0.310, 0.644) | 595 hr |
| Example 5 | Compound 42 | 5.91 | 50 | 8023 | 16.04 | (0.311, 0.643) | 473 hr |
| Comparative Example 1 | Alq3 | 7.45 | 50 | 6102 | 12.2 | (0.309, 0.642) | 237 hr |

The heterocyclic compounds according to embodiments of the present invention have good electrical characteristics, high charge transporting capabilities, light-emission capabilities, high glass transition temperatures ($T_g$), and crystallization prevention characteristics. Thus, the inventive heterocyclic compounds may be used as an electron transporting material or an emitting material for all-color fluorescent and phosphorescent devices, such as red, green, blue, and white fluorescent and phosphorescent devices. Thus, an organic light-emitting device with high-efficiency, low driving voltage, high luminance and long lifespan may be manufactured using the heterocylic compounds.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heterocyclic compound comprising a compound represented by Formula 1 or Formula 2 below:

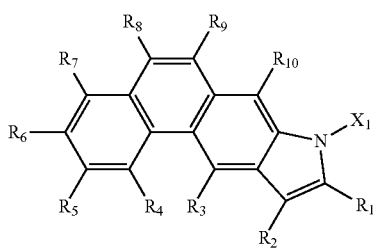

Formula 1

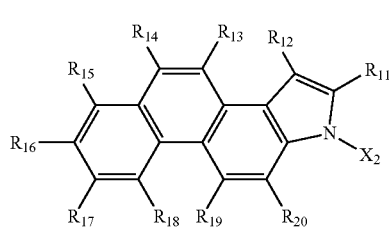

Formula 2 wherein:
each of $X_1$ and $X_2$ is independently selected from the group consisting of substituted and unsubstituted $C_6$-$C_{60}$ aryl groups, and substituted and unsubstituted $C_3$-$C_{60}$ heteroaryl groups,
each of $R_3$-$R_5$, $R_7$-$R_{10}$, $R_{13}$-$R_{15}$, and $R_{17}$-$R_{20}$ is independently selected from the group consisting of hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_6$-$C_{50}$ aryloxy groups, substituted and unsubstituted $C_6$-$C_{50}$ arylthio groups, substituted and unsubstituted $C_6$-$C_{60}$ aryl groups, amino groups substituted with at least one $C_6$-$C_{60}$ aryl group, substituted and unsubstituted $C_3$-$C_{60}$ heteroaryl groups, substituted and unsubstituted $C_6$-$C_{60}$ condensed polycyclic groups, halogen atoms, nitro groups, cyano groups, hydroxyl groups, and carboxyl groups, each of $R_1$, $R_2$, $R_{11}$ and $R_{12}$ is independently a methyl group or a phenyl group, and each of $R_6$ and $R_{16}$ is independently selected from the group consisting of substituted and unsubstituted $C_6$-$C_{60}$ aryl groups, amino groups substituted with at least one $C_6$-$C_{60}$ aryl group, and substituted and unsubstituted $C_3$-$C_{60}$ heteroaryl groups, wherein two or more neighboring substituents selected from $R_3$-$R_5$, $R_7$-$R_{10}$, $R_{13}$-$R_{15}$, and $R_{17}$-$R_{20}$ may optionally combine to form an aromatic ring.

2. The heterocyclic compound of claim 1, wherein $R_6$ or $R_{16}$ is independently selected from the group consisting of:

unsubstituted monocyclic to tetracyclic aryl groups, unsubstituted $C_3$-$C_{60}$ heteroaryl groups, and unsubstituted $C_6$-$C_{50}$ arylamine groups, selected from the group consisting of unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups;

monocyclic to tetracyclic aryl groups selected from the group consisting of phenyl groups, naphthyl groups, biphenyl groups, terphenyl groups, anthracenyl groups, fluorenyl groups, carbazolyl groups, and pyrenyl groups, substituted with at least one substituent selected from the group consisting of $C_1$-$C_5$ alkyl groups, $C_1$-$C_5$ alkoxy groups, cyano groups, amine groups, phenoxy groups, phenyl groups, and halogen groups;

$C_4$-$C_{60}$ heteroaryl groups substituted with at least one substituent selected from the group consisting of $C_1$-$C_5$ alkyl groups, $C_1$-$C_5$ alkoxy groups, cyano groups, amine groups, phenoxy groups, phenyl groups, halogen groups and $C_5$-$C_{10}$ heteroaryl groups; and $C_6$-$C_{50}$ arylamine groups substituted with at least one substituent selected from the group consisting of $C_1$-$C_5$ alkyl groups, $C_1$-$C_4$ alkoxy groups, cyano groups, amine groups, phenoxy groups, phenyl groups, and halogen groups.

3. The heterocyclic compound of claim 1, wherein $X_1$ or $X_2$ is selected from the group consisting of:

unsubstituted monocyclic to tetracyclic aryl groups selected from the group consisting of unsubstituted phenyl groups, unsubstituted naphthyl groups, unsubstituted biphenyl groups, unsubstituted terphenyl groups, unsubstituted anthracenyl groups, unsubstituted fluorenyl groups, unsubstituted carbazolyl groups, and unsubstituted pyrenyl groups;

unsubstituted $C_3$-$C_{60}$ heteroaryl groups;

monocyclic to tetracyclic aryl groups selected from the group consisting of phenyl groups, naphthyl groups, biphenyl groups, terphenyl groups, anthracenyl groups, fluorenyl groups, carbazolyl groups, and pyrenyl groups, substituted with at least one substituent selected from the group consisting of $C_1$-$C_5$ alkyl groups, $C_1$-$C_5$ alkoxy groups, cyano groups, amine groups, phenoxy groups, phenyl groups, and halogen groups; and $C_4$-$C_{60}$ heteroaryl groups substituted with at least one substituent selected from $C_1$-$C_5$ alkyl groups, $C_1$-$C_5$ alkoxy groups, cyano groups, amine groups, phenoxy groups, phenyl groups, halogen groups and $C_5$-$C_{10}$ heteroaryl groups.

4. The heterocyclic compound of claim 1, wherein the compound represented by Formula 1 or Formula 2 comprises a compound selected from the group consisting of Compounds 10, 17, 27, 33, and 42:

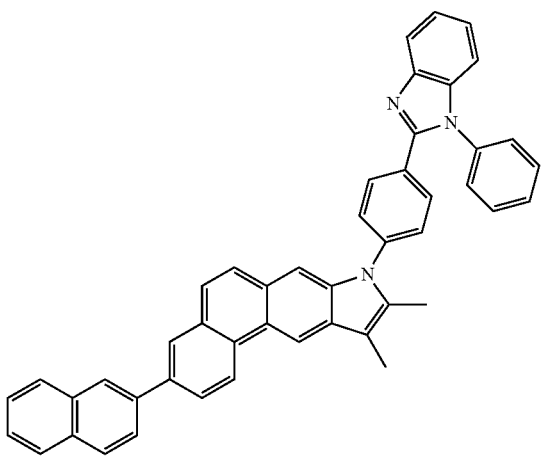

10

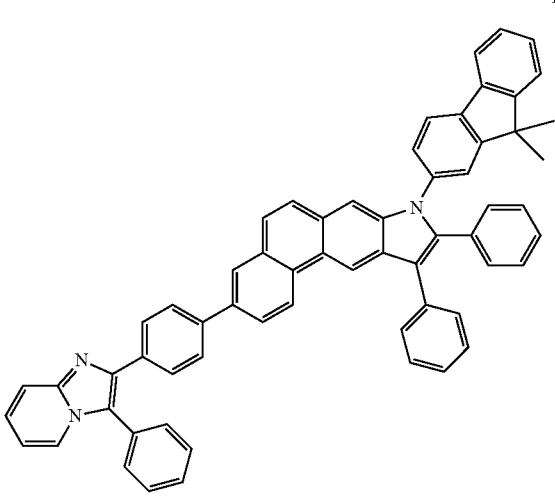

17

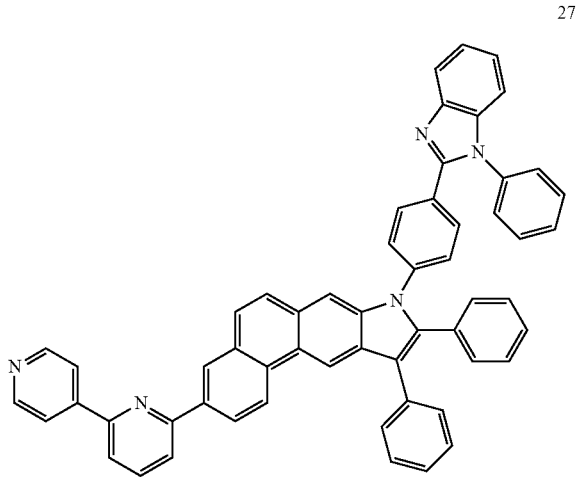

27

-continued

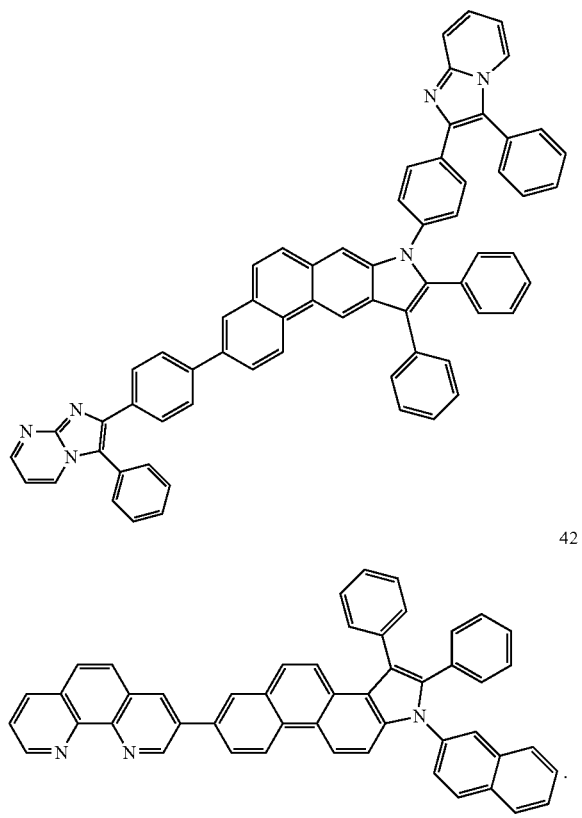

5. An organic light-emitting device comprising:
a first electrode;
a second electrode; and
an organic layer between the first electrode and the second electrode, wherein the organic layer comprises at least one layer comprising the heterocyclic compound of claim 1.

6. The organic light-emitting device of claim 5, wherein the organic layer comprises an electron injection layer or an electron transport layer.

7. The organic light-emitting device of claim 5, wherein the organic layer comprises a single film having both an electron injection function and an electron transport function.

8. The organic light-emitting device of claim 5, wherein the organic layer comprises an emission layer.

9. The organic light-emitting device of claim 5, wherein the organic layer comprises an emission layer, and the heterocyclic compound is a host for a fluorescent or phosphorescent device.

10. The organic light-emitting device of claim 5, wherein the organic layer comprises an emission layer, and the heterocyclic compound is a fluorescent dopant.

11. The organic light-emitting device of claim 5, wherein the organic layer comprises an emission layer, and an electron injection layer or an electron transport layer, wherein the emission layer comprises an anthracene compound or an arylamine compound or a styryl compound.

12. The organic light-emitting device of claim 5, wherein the organic layer comprises an emission layer, and an electron injection layer or an electron transport layer, wherein the emission layer comprises a red emission layer, a green emission layer, a blue emission layer, or a white emission layer that comprises a phosphorescent compound.

13. The organic light-emitting device of claim 5, wherein the organic layer comprises at least one layer selected from the group consisting of a hole injection layer, a hole transport layer, an electron blocking layer, an emission layer, a hole blocking layer, an electron transport layer, and an electron injection layer.

14. The organic light-emitting device of claim 13, wherein the organic light-emitting device has a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

15. A flat panel display device comprising the organic light-emitting device of claim 5, wherein the first electrode of the organic light-emitting device is electrically connected to a source electrode or a drain electrode of a thin-film transistor.

16. An organic light-emitting device comprising:
a first electrode;
a second electrode; and
an organic layer between the first electrode and the second electrode,
wherein the organic layer comprises at least one layer comprising the heterocyclic compound of claim 1, the at least one layer being formed using a wet process.

17. The heterocyclic compound of claim 1, wherein the compound represented by Formula 1 or Formula 2 comprises a compound selected from the group consisting of Compounds 1 through 52:

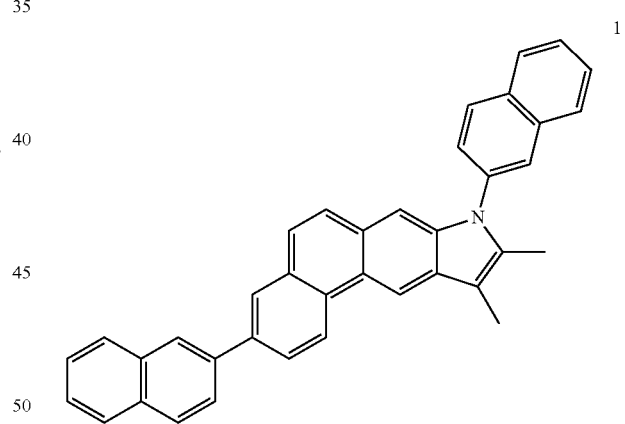

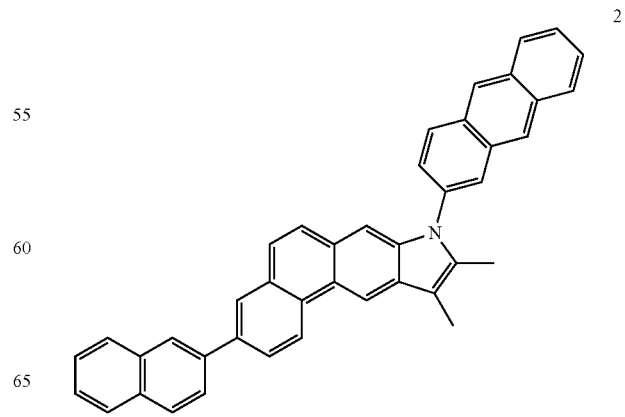

3
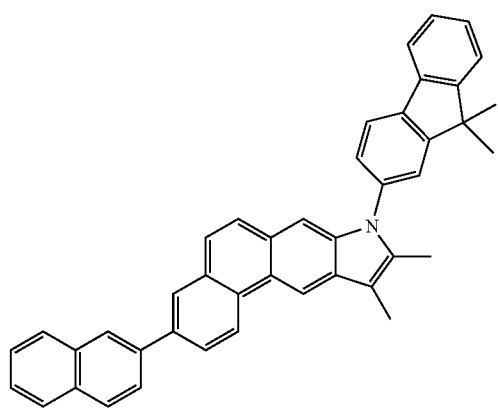
4
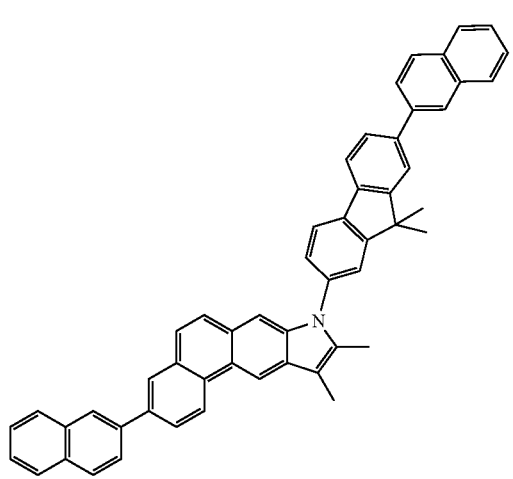
5
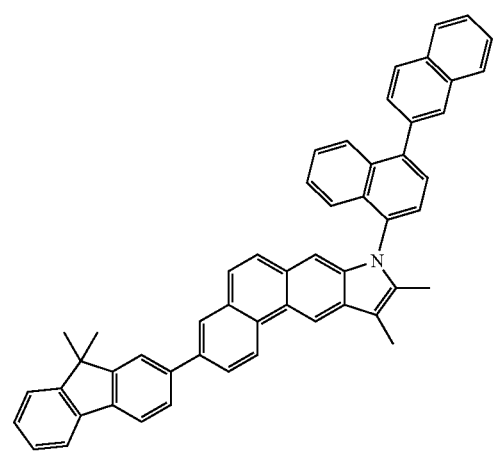
6
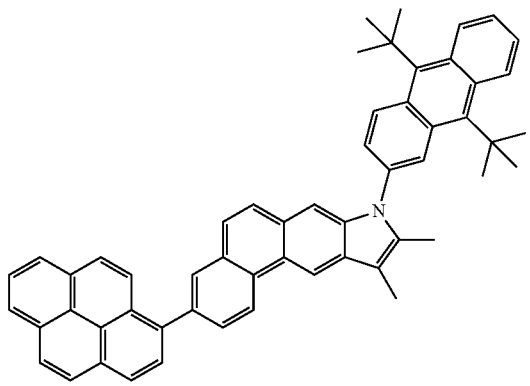
7
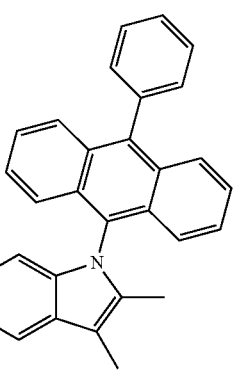
8
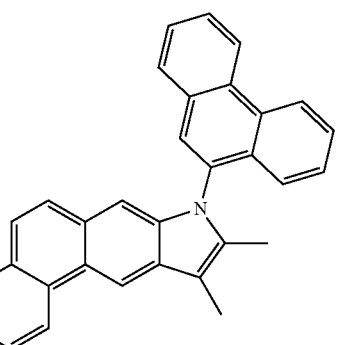

9
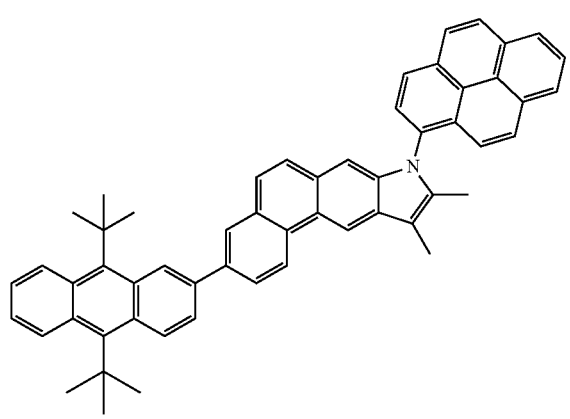
10
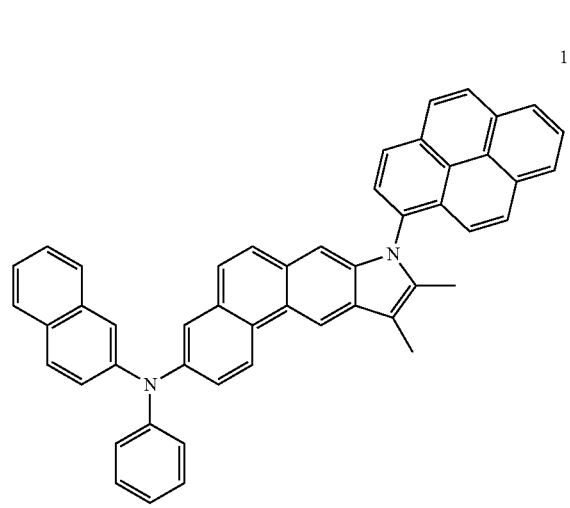
11
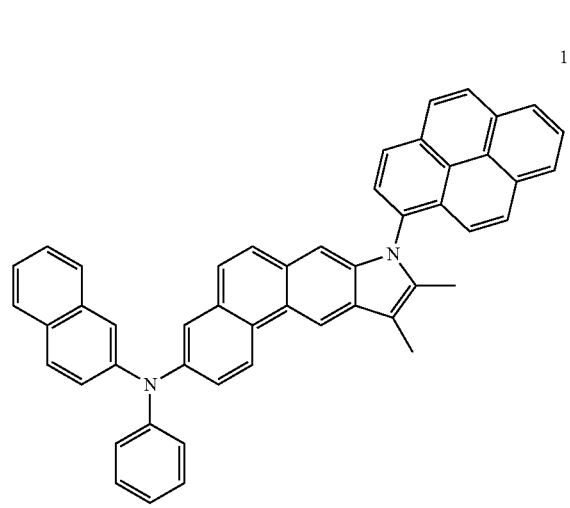
12
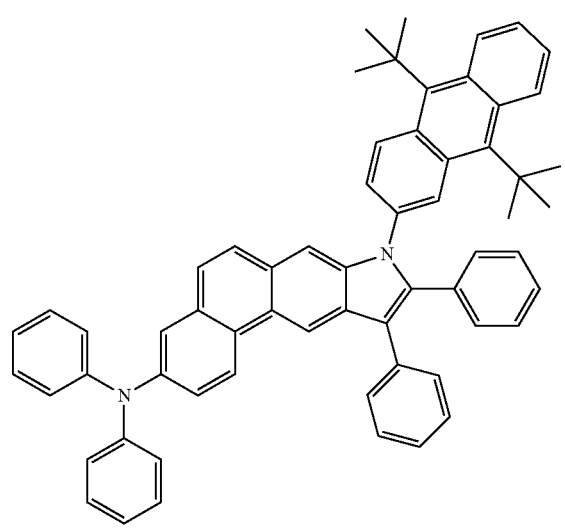
13
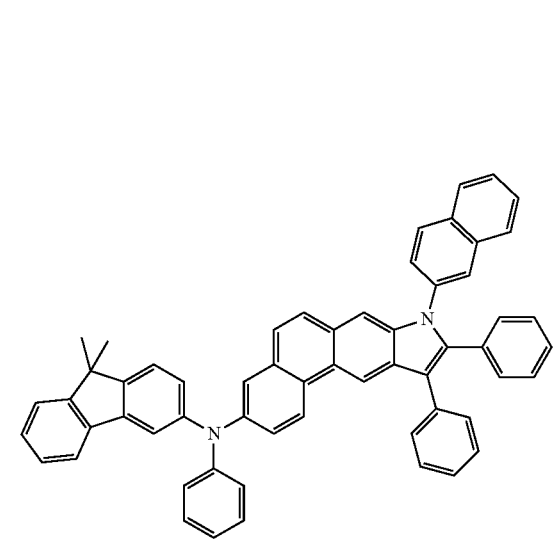
14
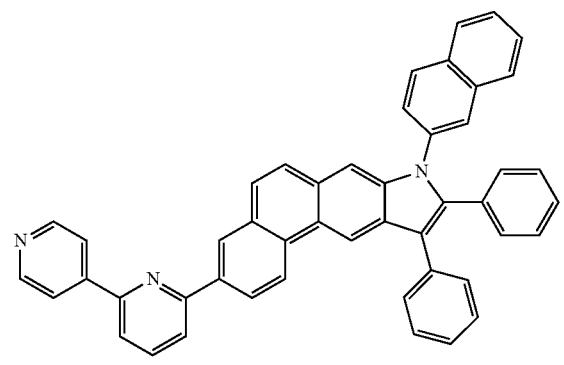

-continued
15
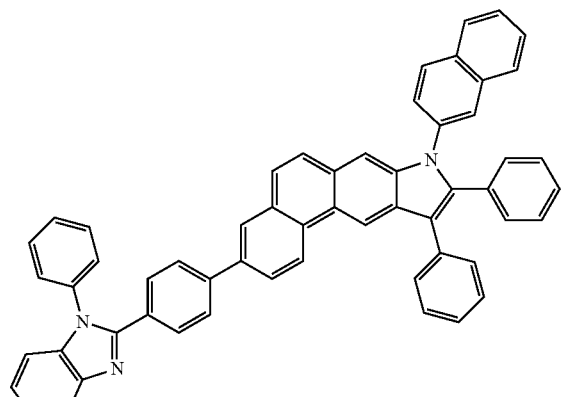
16
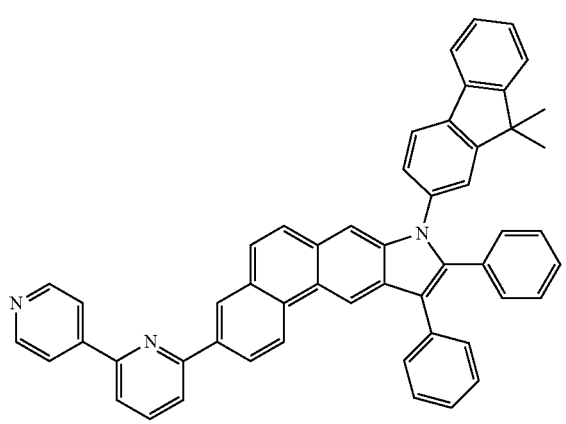
17
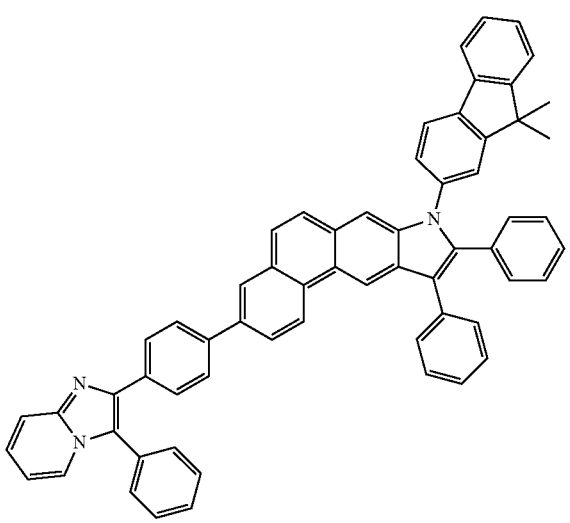
-continued
18
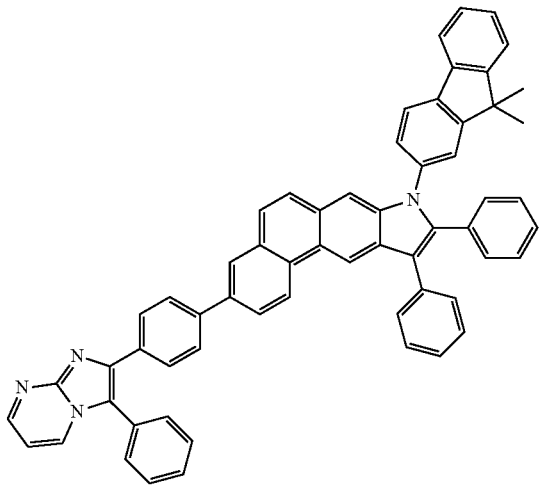
19
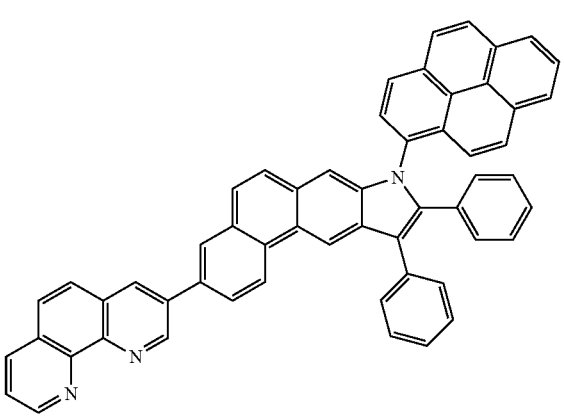
20
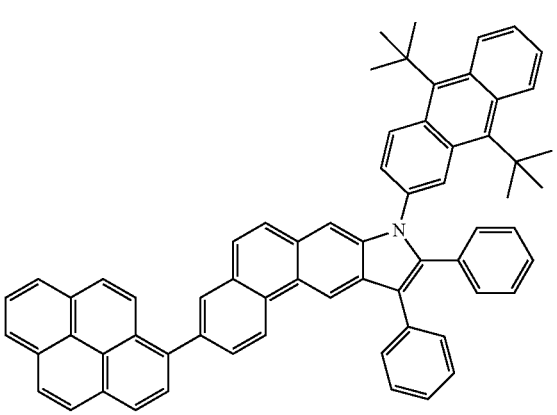

61

-continued

21

22

23

62

-continued

24

25

26

27
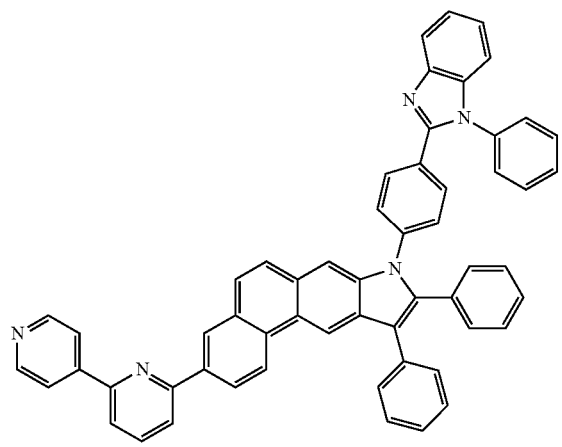
28
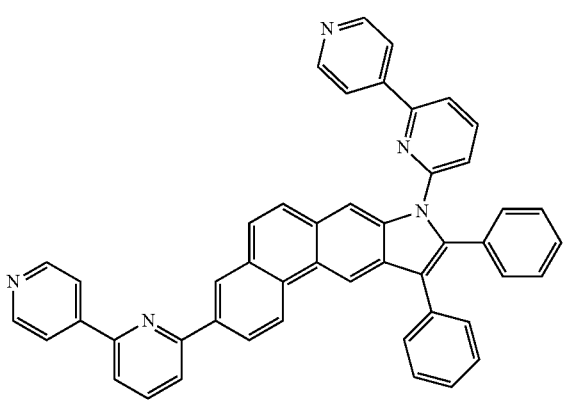
29
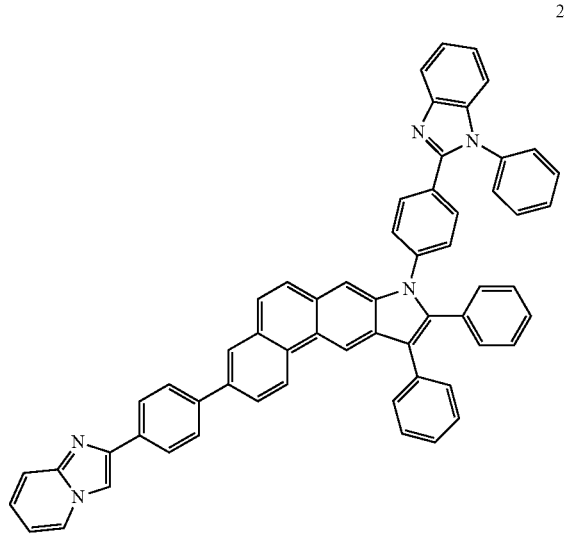
30
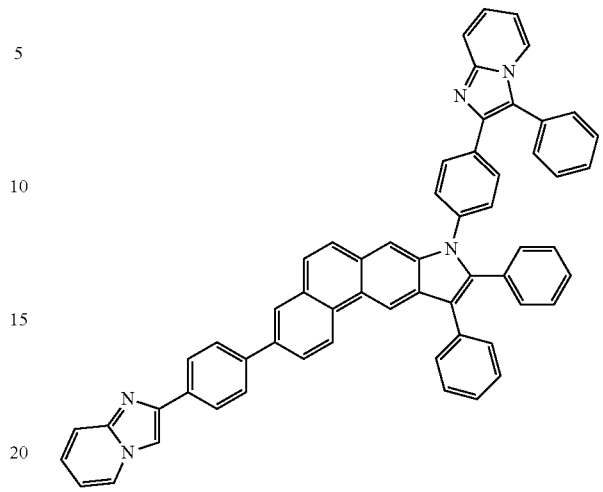
31
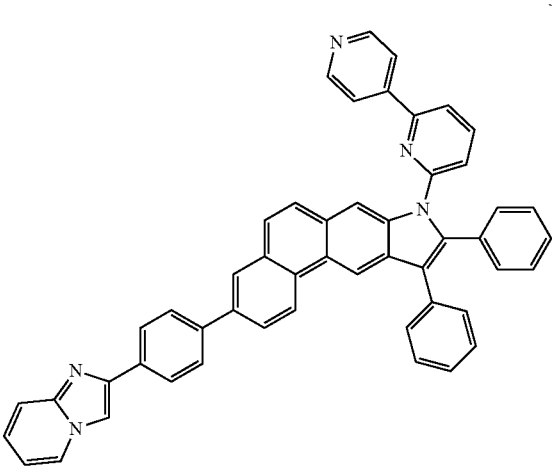
32
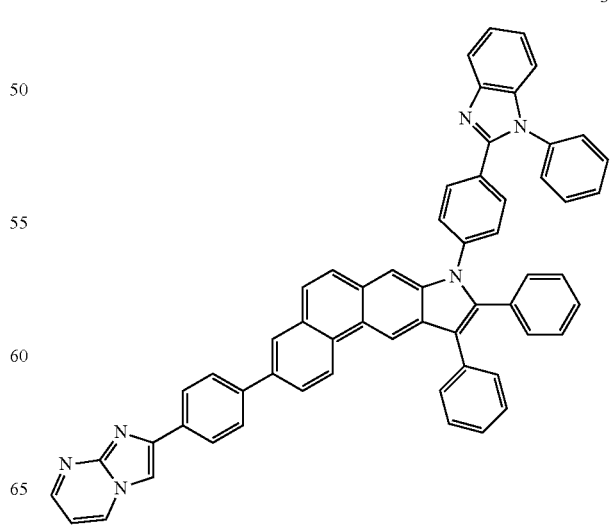

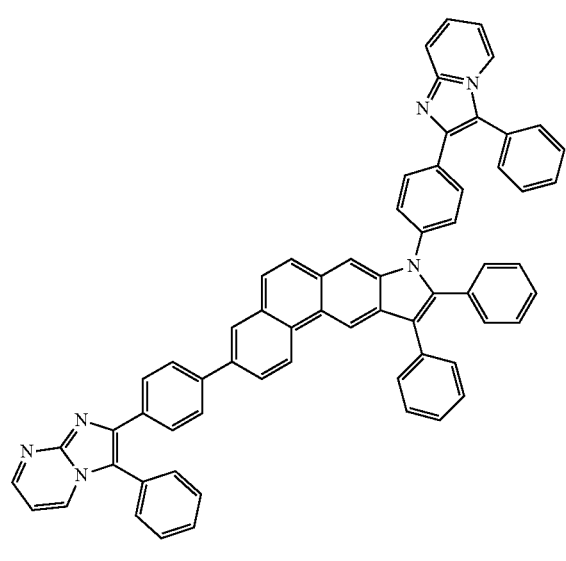
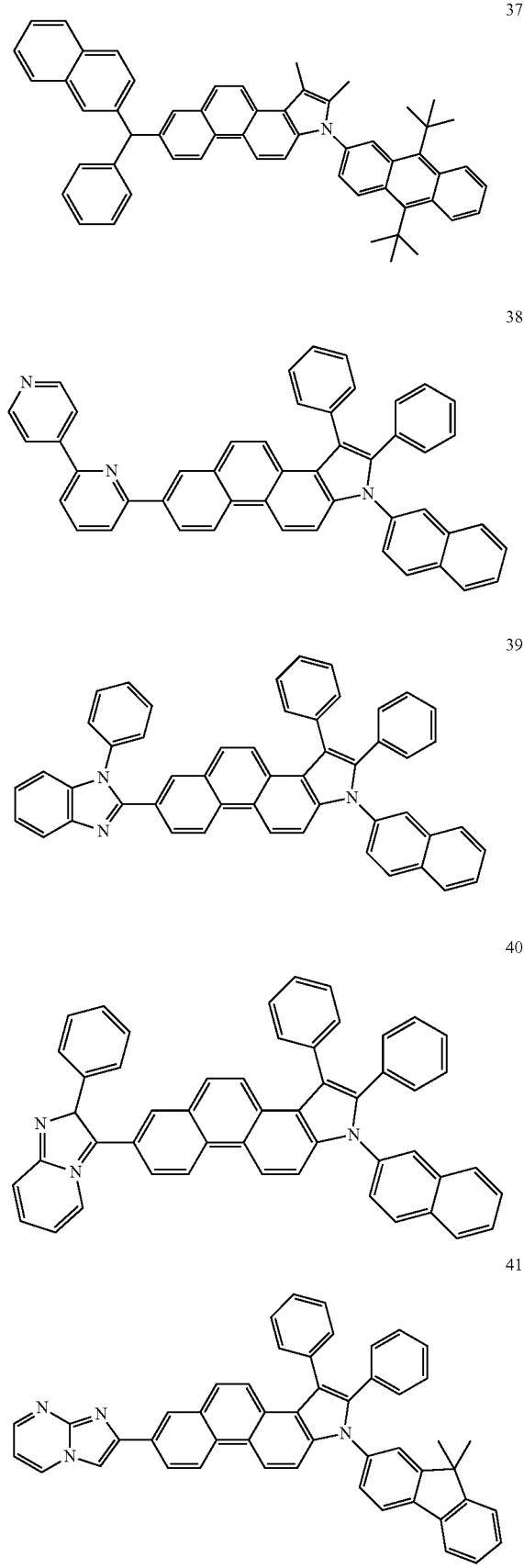

42
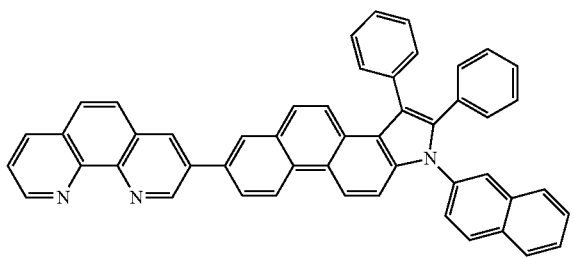
43
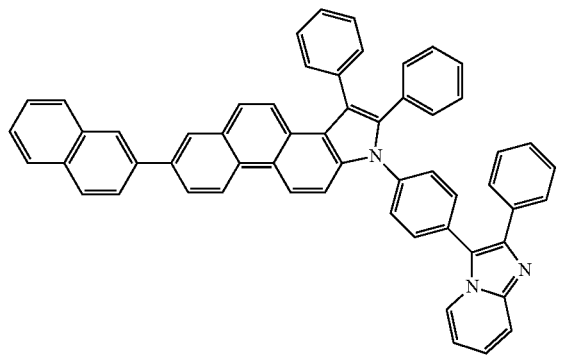
44
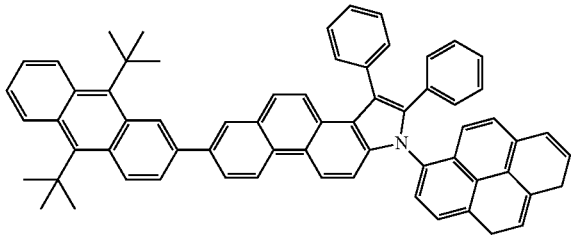
45
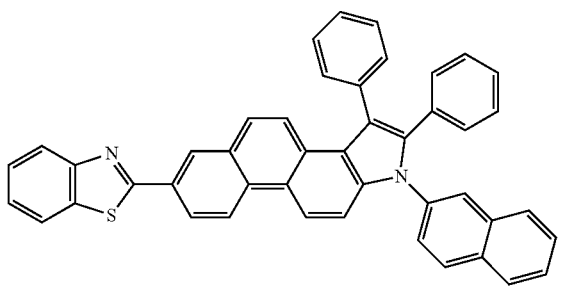
46
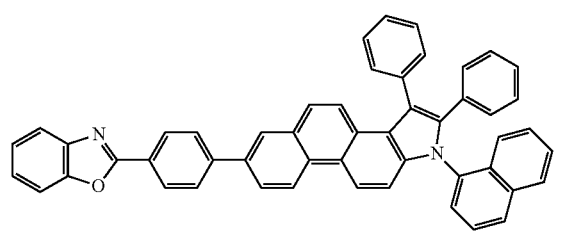
47
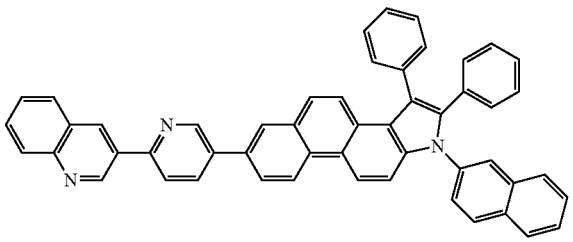
48
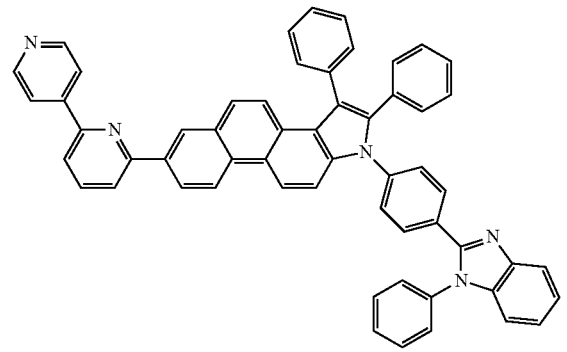
49
50

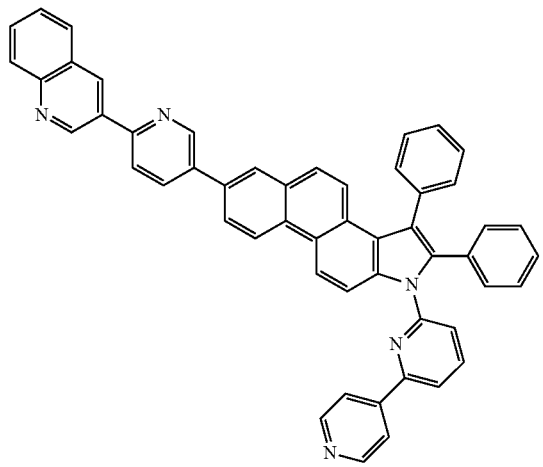
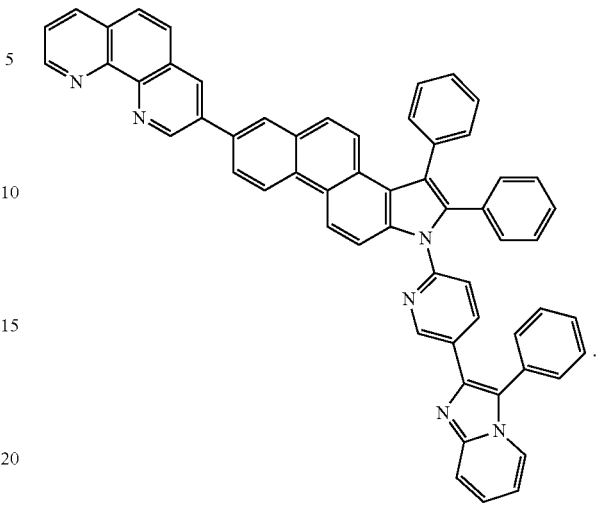
* * * * *